(12) United States Patent
Rughani et al.

(10) Patent No.: US 11,819,560 B2
(45) Date of Patent: *Nov. 21, 2023

(54) COSMETIC COMPOSITIONS, KITS THEREOF, AND METHODS FOR MAKING AND USING THE SAME

(71) Applicant: L'OREAL, Paris (FR)

(72) Inventors: Ronak Rughani, Edison, NJ (US); Cho-Cho Khine, Bridgewater, NJ (US)

(73) Assignee: L'OREAL, Paris (FR)

(*) Notice: Subject to any disclaimer, the term of this patent is extended or adjusted under 35 U.S.C. 154(b) by 137 days.

This patent is subject to a terminal disclaimer.

(21) Appl. No.: 17/007,832

(22) Filed: Aug. 31, 2020

(65) Prior Publication Data

US 2022/0062129 A1 Mar. 3, 2022

(51) Int. Cl.
| | |
|---|---|
| *A61K 8/36* | (2006.01) |
| *A61K 8/34* | (2006.01) |
| *A61K 8/40* | (2006.01) |
| *A61K 8/92* | (2006.01) |
| *A61Q 5/12* | (2006.01) |
| *A61Q 5/00* | (2006.01) |

(52) U.S. Cl.
CPC .............. *A61K 8/361* (2013.01); *A61K 8/345* (2013.01); *A61K 8/40* (2013.01); *A61K 8/92* (2013.01); *A61K 2800/31* (2013.01); *A61Q 5/002* (2013.01); *A61Q 5/12* (2013.01)

(58) Field of Classification Search
CPC .......... A61K 8/42; A61K 8/345; A61K 8/362; A61K 8/92; A61Q 5/12
See application file for complete search history.

(56) References Cited

U.S. PATENT DOCUMENTS

| 10,137,073 B2 | 11/2018 | De Lemos et al. |
| 2002/0019547 A1 | 2/2002 | Tuloup et al. |

(Continued)

FOREIGN PATENT DOCUMENTS

| CA | 3107391 A1 | 2/2020 |
| CN | 106176454 A | 12/2016 |

(Continued)

OTHER PUBLICATIONS

International Search Report and Written opinion dated Dec. 22, 2021 for corresponding PCT Application No. PCT/US2021/047078.

(Continued)

*Primary Examiner* — Kyung S Chang
(74) *Attorney, Agent, or Firm* — POLSINELLI PC

(57) ABSTRACT

Cosmetic compositions, kits thereof, and methods of making and using such cosmetic compositions. The cosmetic compositions typically include about 20 to about 95 wt. % of a polyol; about 5 to about 70 wt. % of one or more monoalcohols having from 2 to 6 carbon atoms; about 0.1 to about 10 wt. % of one or more cationic surfactants; about 0.1 to about 20 wt. % of one or more fatty compounds; and about 1 to about 15 wt. % of a combination of a urea compound and citric acid, wherein all weight percentages are based on the total weight of the cosmetic composition. The cosmetic compositions have a weight ratio of polyol to monoalcohol(s) that is from 20:1 to 1:20. Additionally, the cosmetic compositions typically have a mole ratio of citric acid to urea compound of that is about 10:0.5 to about 0.5:10.

23 Claims, 11 Drawing Sheets

(56) References Cited

U.S. PATENT DOCUMENTS

| | | |
|---|---|---|
| 2002/0081271 A1 | 6/2002 | Martin et al. |
| 2002/0137795 A1 | 9/2002 | Martin et al. |
| 2003/0108504 A1* | 6/2003 | Sako ........................ A61K 8/39 |
| | | 424/70.31 |
| 2003/0224060 A1 | 12/2003 | Simonnet et al. |
| 2007/0225360 A1 | 9/2007 | Pinnell et al. |
| 2008/0118449 A1 | 5/2008 | Ronlan |
| 2008/0160110 A1 | 7/2008 | Kang et al. |
| 2009/0286874 A1 | 11/2009 | Pinnell et al. |
| 2011/0146699 A1 | 6/2011 | Saute et al. |
| 2019/0282478 A1 | 9/2019 | Pesaro et al. |
| 2020/0069025 A1 | 3/2020 | Ferebee Maher et al. |
| 2020/0129405 A1 | 4/2020 | Mitchell et al. |

FOREIGN PATENT DOCUMENTS

| | | |
|---|---|---|
| CN | 109498494 A | 3/2019 |
| EP | 2608766 B1 | 1/2015 |

OTHER PUBLICATIONS

Preliminary Search Report and Written Opinion dated Jul. 8, 2021 for corresponding French Application No. FR2010608.

\* cited by examiner

COSMETIC COMPOSITIONS, KITS THEREOF, AND METHODS FOR MAKING AND USING THE SAME

FIELD OF THE DISCLOSURE

The present disclosure relates to cosmetic compositions and kits thereof. Aspects of the present disclosure also relate to methods for making such cosmetic compositions and methods of using such cosmetic compositions.

BACKGROUND

Consumers desire new and improved compositions for treating, caring for, and/or conditioning keratinous substances, such as skin or hair. Hair and skin are exposed to intrinsic and extrinsic influences such as environmental factors, mechanical factors, chemical factors, heat, and aging.

For example, the action of external atmospheric agents such as light and bad weather, and also by heat, mechanical or chemical treatments, such as brushing, combing, dyeing, bleaching, permanent-waving and/or relaxing, blow-drying, flat ironing, or even repeated washing can damage and weaken hair fibers. Over time, hair may become dry, coarse, brittle or dull, especially in fragile areas, and more particularly at the ends, resulting in split ends.

Thus, to overcome these drawbacks, it is common practice to resort to haircare products using compositions intended to condition the hair, giving it satisfactory cosmetic properties, especially in terms of smoothness, sheen, softness, suppleness, lightness, a natural feel and good disentangling properties. For example, hair care compositions, such as hair conditioner and/or treatment compositions, may be used before or after the hair has been washed with shampoo and/or subjected to a chemical treatment in order to improve or return to the hair its natural luster, shine, and softness, or to improve the feel, appearance, and manageability of hair.

It is understood that different forms of haircare and skin care compositions can provide different benefits.

However, there is still a need for providing improved hair manageability, for example, improved hair alignment, reduced unwanted volume (especially reduced frizz), and increased shine. There is also a need to develop cosmetic products that can impart other benefits at the same time in addition to caring and conditioning benefits, such as styling, volume, shaping, curl definition (for curly or wavy hair), and restylability or reshaping (without the need to reapply the product).

SUMMARY OF THE DISCLOSURE

Aspects of the present disclosure relate to cosmetic compositions and kits thereof. Further aspects of the present disclosure relate to methods for making such cosmetic compositions and methods of using such cosmetic compositions on keratinous substrates such as hair and skin.

When the keratinous substrate is hair, in particular, hair on the human head, the cosmetic compositions of the present disclosure simultaneously achieve both surface and deep repair to hair. The inventors surprisingly discovered that certain compounds and their associations in specific weight and/or mole ratios enable the cosmetic compositions to significantly improve durability and resistance to thermal degradation of hair. Additionally, the inventors recognized that forming a deep eutectic solvent system ("DES") system from certain compounds and their associations in specific weight and/or mole ratios before forming the cosmetic composition—e.g., by forming a DES system before inclusion into a base composition comprising the cosmetic composition—enhances the benefits achieved by the cosmetic composition.

Additionally, the cosmetic compositions may be formulated to form a lamellar phase when the cosmetic composition is mixed with extraneous water. Without being limited to any specific theory, it is believed that the lamellar structures formed by the cosmetic compositions may further enhance the benefits achieved by the cosmetic compositions and, particularly, improve the manageability of hair and/or reduce frizz.

The cosmetic compositions typically include:
(a) about 20 to about 95 wt. % of a polyol;
(b) about 5 to about 70 wt. % of one or more monoalcohols having from 2 to 6 carbon atoms;
  wherein the weight ratio of the polyol to the monoalcohol(s) (polyol:monoalcohol(s)) is from 20:1 to 1:20;
(c) about 0.1 to about 10 wt. % of one or more cationic surfactants;
(d) about 0.1 to about 20 wt. % of one or more fatty compounds; and
(e) about 1 to about 15 wt. % of a combination of:
  (i) a urea compound, and
  (ii) citric acid, wherein a mole ratio of the citric acid of
    (i) to the urea compound of
    (ii) is about 10:0.5 to about 0.5:10, and all weight percentages are based on the total weight of the cosmetic composition.

In some case, the amount of the combination of the urea compound and the citric acid present in the cosmetic composition is about 3 to about 7 wt. %. In an embodiment, the mole ratio of citric acid of (i) to the urea compound of (ii) may range from about 5:1 to about 1:5. The urea compound in the cosmetic composition may be dimethyl urea, a hydroxyethyl urea, urea or mixtures thereof. Preferably, the combination of the urea compound and the citric acid may be added into the cosmetic composition as a deep eutectic solvent.

The cosmetic composition may be a solubilized, non-emulsified composition until applied to a wet or damp keratinous substrate, such as hair or skin, or placed on contact with water, whereupon the composition forms a lamellar phase in situ. The cosmetic composition may be include polyols chosen from ethylene glycol, propylene glycol, butylene glycol, hexylene glycol, pentylene glycol, diethylene glycol, dipropylene glycol, 1,3 propanediol, glycerin, polyethylene glycols, and a mixture thereof.

Examples of cationic surfactants for the cosmetic composition include cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, stearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, and a mixture thereof.

The cosmetic compositions preferably includes a fatty compound chosen from a fatty alcohol, a fatty ester, a fatty ether, a fatty acid, a wax, an oil, a derivative thereof, and a mixture thereof. In some cases, the fatty compound is a fatty carbonate esters chosen from dialkyl carbonates of formula: $R_1O(C=O)R_2$, wherein $R_1$ and $R_2$ are independently linear or branched, saturated or unsaturated alkyl chains having 1 to 30 carbon atoms, or having 2 to 28 carbon atoms, or having 4 to 25 carbon atoms, or having 6 to 22 carbon atoms, preferably one or more fatty carbonates selected from C14-15 dialkyl carbonate, dicaprylyl carbonate, diethyl carbonate, dihexyl carbonate, diethylhexyl carbonate, dimethoxyphenyl phenyloxyethyl ethylcarbonate, dimethyl carbonate, dipropyl carbonate, dipropylheptyl carbonate, dioctyl carbonate, and a mixture thereof. In additional cases, the fatty compound is a fatty ester chosen from cetyl ester, purcellin oil (cetearyl octanoate), isopropyl myristate, isopropyl palmitate, $C_{12}$-$C_{15}$ alkyl benzoate, 2-ethylphenyl benzoate, isopropyl lanolate, hexyl laurate, diisopropyl adipate, isononyl isononanoate, oleyl erucate, 2-ethylhexyl palmitate, isostearyl isostearate, diisopropyl sebacate, octanoates, decanoates or ricinoleates of alcohols or polyalcohols, hydroxylated esters, dicaprylyl carbonate, pentaerythritol esters, diisostearyl malate, neopentyl glycol dioctanoate, dibutyl sebacate, di-$C_{12-13}$ alkyl malate, dicetearyl dimer dilinoleate, dicetyl adipate, diisocetyl adipate, diisononyl adipate, diisostearyl dimer dilinoleate, diisostearyl fumarate, and a mixture thereof.

Additionally or alternatively, the fatty compound may be a fatty alcohol chosen from decyl alcohol, undecyl alcohol, dodecyl alcohol, myristyl alcohol, lauryl alcohol, cetyl alcohol, stearyl alcohol, cetearyl alcohol, isostearyl alcohol, isocetyl alcohol, behenyl alcohol, linalool, oleyl alcohol, cis-4-t-butylcyclohexanol, isotridecyl alcohol, myricyl alcohol, and a mixture thereof. The fatty compound may be a fatty ether chosen from olyoxyethylene cetyl/stearyl ether, polyoxyethylene cholesterol ether, polyoxyethylene laurate or dilaurate, polyoxyethylene stearate or distearate, polyoxyethylene lauryl or stearyl ether, dicaprylyl ether, dicetyl ether distearyl ether, dodecyl ether, dilauryl ether, dimyristyl ether, diisononyl ether, and a mixture thereof. In at least one instance, the cosmetic composition is substantially free of water. In at least one further instance, the cosmetic compositions is free of water.

Aspects of the disclosure relate to methods for producing cosmetic compositions. The methods for producing cosmetic compositions typically include:
(I) producing a deep eutectic solvent system comprising:
  (i) citric acid, and
  (ii) urea compound,
    wherein a mole ratio of the citric acid of (i) to the urea compound of (ii) is about 10:0.5 to about 0.5:10; and
(II) adding the deep eutectic solvent system of (I) to a base composition comprising:
  (a) about 20 to about 95 wt. %, based on the weight of the base composition, of a polyol;
  (b) about 5 to about 70 wt. %, based on the weight of the base composition, of one or more monoalcohols having from 2 to 6 carbon atoms;
    wherein the weight ratio of the polyol to the monoalcohol(s) (polyol:monoalcohol(s)) is from 20:1 to 1:20;
  (c) about 0.1 to about 10 wt. %, based on the weight of the base composition, of one or more cationic surfactants; and
  (d) about 0.1 to about 20 wt. %, based on the weight of the base composition, of one or more fatty compounds.

The method may further include forming the deep eutectic solvent (DES) system of (I) by mixing the citric acid and urea compound(s) in certain ratios, e.g., as discussed herein. In some cases, the DES system may be formed at room temperatures, e.g., when the citric acid and urea compounds mix as liquids at room temperature. In other cases, the method also includes heating a mixture/combination of the citric acid and the urea compound to a temperature of about 70° C. to about 90° C.

According to further aspects of the disclosure, provided are methods for treating hair. The methods for treating hair typically include:
(I) optionally, applying a shampoo to hair;
(II) optionally, rinsing the hair to remove at least a portion of the shampoo;
(III) applying a cosmetic composition comprising:
  (a) about 20 to about 95 wt. % of a polyol;
  (b) about 5 to about 70 wt. % of one or more monoalcohols having from 2 to 6 carbon atoms;
    wherein the weight ratio of the polyol to the monoalcohol(s) (polyol:monoalcohol(s)) is from 20:1 to 1:20;
  (c) about 0.1 to about 10 wt. % of one or more cationic surfactants;
  (d) about 0.1 to about 20 wt. % of one or more fatty compounds; and
  (e) about 1 to about 15 wt. % of a combination of:
    (i) citric acid, and
    (ii) a urea compound,
      wherein a mole ratio of the citric acid of (i) to the urea compound of (ii) is about 10:0.5 to about 0.5:10, and all weight percentages are based on the total weight of the cosmetic composition; and
(IV) optionally, rinsing the hair to remove at least a portion of the cosmetic composition.

BRIEF DESCRIPTION OF THE DRAWINGS

Implementation of the present technology will now be described, by way of example only, with reference to the attached figures, wherein.

Figure 1:
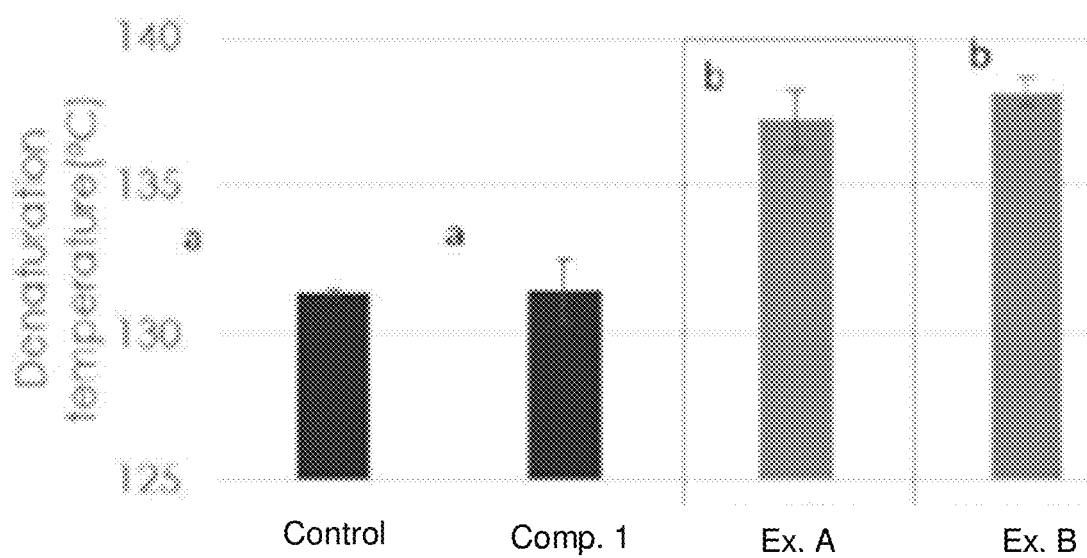
FIG. 1 is a bar graph showing the denaturation temperature of hair swatches after comparative compositions and exemplary cosmetic compositions in accordance with aspects of the disclosure.

It should be understood that the various aspects are not limited to the arrangements and instrumentality shown in the drawings.

DETAILED DESCRIPTION OF THE DISCLOSURE

Aspects of the present disclosure relate to cosmetic compositions and kits thereof. Further aspects of the present disclosure relate to methods for making such cosmetic compositions and methods of using such cosmetic compositions on keratinous substrates such as hair and skin.

When the keratinous substrate is hair, in particular, hair on the human head, the cosmetic compositions of the present disclosure simultaneously achieve both surface and deep repair to hair. The inventors surprisingly discovered that certain compounds and their associations in specific weight and/or mole ratios enable the cosmetic compositions to significantly improve durability and resistance to thermal degradation of hair. Additionally, the inventors recognized that forming a deep eutectic solvent system ("DES") system from certain compounds and their associations in specific weight and/or mole ratios before forming the cosmetic composition—e.g., by forming a DES system before inclusion into base composition comprising the cosmetic composition—enhances the benefits achieved by the cosmetic composition.

Additionally, the cosmetic compositions may be capable of self-association typically through hydrogen bond interactions, which may enable the cosmetic compositions to reinforce and/or strengthen hair, particularly damaged hair. In some embodiments, cosmetic compositions restore damaged hair.

The cosmetic compositions disclosed herein, when used on hair, may also advantageously reduce frizz and/or increased hair manageability. Without being limited to any specific theories, the inventors believe that the cosmetic compositions, and particularly cosmetic compositions containing certain deep eutectic solvent systems, may disrupt the weak bonds in hair associated with moisture absorbed atmosphere to reduce frizz and increase the manageability of the hair.

The cosmetic compositions may be formulated to form a lamellar phase when the cosmetic composition is mixed with extraneous water. Without being limited to any specific theory, it is believed that the lamellar structures formed by the cosmetic compositions may further enhance the benefits achieved by the cosmetic compositions and, particularly, improve the manageability of hair and/or reduce frizz.

The cosmetic compositions may also provide a unique sensorial and consumer experience. For example, the cosmetic compositions may be heat and/or shear activated, such that the compositions undergo a sensorial and/or tactile changes. In some instances, the cosmetic compositions transition from exhibiting a more solid-like behavior to exhibiting a more liquid-like behavior in the presence of heat activation and/or shear, such as provided by a user rubbing the cosmetic composition between his or her hands or applying the cosmetic composition during a warm shower or bath. In some instances, the viscosity of the cosmetic composition may transition from a viscosity of about 10 to about 500 Pas at a temperature of 24° C. to a reduced viscosity of less than 100 Pas at a temperature of 40° C. as measured with LV 04 Spindle on a Brookfield DV2T viscometer at a range of 1 to 10 rpm after 90 seconds.

The cosmetic compositions typically include:
(a) about 20 to about 95 wt. % of a polyol;
(b) about 5 to about 70 wt. % of one or more monoalcohols having from 2 to 6 carbon atoms;
    wherein the weight ratio of the polyol to the monoalcohol(s) (polyol:monoalcohol(s)) is from 20:1 to 1:20;
(c) about 0.1 to about 10 wt. % of one or more cationic surfactants;
(d) about 0.1 to about 20 wt. % of one or more fatty compounds; and
(e) about 1 to about 15 wt. % of a combination of:
    (i) citric acid, and
    (ii) a urea compound,
        wherein a mole ratio of the citric acid of (i) to the urea compound of
    (ii) is about 10:0.5 to about 0.5:10, and all weight percentages are based on the total weight of the cosmetic composition.

The cosmetic composition may be formulated to have an amount of polyol to an amount of monoalcohols in a ratio (i.e. total polyols:total monoalcohols) of 20:1 to 1:20. For example, the weight ratio of the amount of polyols to the amount of monoalcohols having from 2 to 6 carbon atoms may be from 20:1 to 1:20, 18:1 to 1:20, 15:1 to 1:20, 10:1 to 1:20, 7:1 to 1:20, 6:1 to 1:20, 5:1 to 1:20, 4:1 to 1.1:20, 20:1 to 1:18, 20:1 to 1:15, 20:1 to 1:10, 20:1 to 1:7, 20:1 to 1:6, 20:1 to 1:5, 20:1 to 1:4, including ranges and sub-ranges therebetween (e.g., 5:1 to 1:5, 4:1 to 1:4, 5:1 to 1:1, etc.). In at least one embodiment, the cosmetic composition is formulated such that the total amount of polyols is greater than the total amount of monoalcohols. In at least another instance, the cosmetic composition is formulated such that the total amount of glycol is greater than the total amount of monoalcohols.

The cosmetic composition may be formulated to have a weight ratio of the citric acid of (i) to the urea compound of (ii) may be about 12:0.5 to about 0.5:12. In some instances, the cosmetic composition may be formulated to have a weight ratio of citric acid to urea compound(s) of about 11:1 to about 1:11, about 10:1 to about 1:10, about 9:1 to about 1:9, about 9:1 to about 1:1, about 9:1 to about 3:2, about 8:1 to about 0.5:10, about 7:1 to about 0.5:10, about 6:1 to about 0.5:10, about 5:1 to about 0.5:10, about 4:1 to about 0.5:10, about 3:1 to about 0.5:10; 10:1 to about 1:10, about 9:1 to about 1:10, about 8:1 to about 1:10, about 7:1 to about 1:10, about 6:1 to about 1:10, about 5:1 to about 1:10, about 4:1 to about 1:10, about 3:1 to about 1:10; 10:1 to about 2:10, about 9:1 to about 2:10, about 8:1 to about 2:10, about 7:1 to about 2:10, about 6:1 to about 2:10, about 5:1 to about 2:10, about 4:1 to about 2:10, about 3:1 to about 2:10; about 10:1 to about 2:8, about 9:1 to about 2:8, about 8:1 to about 2:8, about 7:1 to about 2:8, about 6:1 to about 2:8, about 5:1 to about 2:8, about 5:1 to about 3:2, about 4:1 to about 3:2, about 4:1 to about 2:8, about 3:1 to about 2:8; about 10:1 to about 2:6, about 9:1 to about 2:6, about 8:1 to about 2:6, about 7:1 to about 2:6, about 6:1 to about 2:6, about 5:1 to about 2:6, about 4:1 to about 2:6, about 3:1 to about 2:6; about 3:1 to about 1:10, about 3:1 to about 1:9, about 3:1 to about 1:8, about 3:1 to about 1:7, about 3:1 to about 1:6, about 3:1 to about 2:10, about 3:1 to about 2:9, about 3:1 to about 2:8, about 3:1 to about 2:7, about 3:1 to about 2:6, about 3:1 to about 2:5, about 3:1 to about 2:4, or about 3:1 to about 2:3, about 2:1 to about 2:10, about 1:1 to about 2:10, about 3:1 to about 2:9, about 3:1 to about 2:8, about 3:1 to about 2:7, about 3:1 to about 2:6, about 3:1 to about 2:5, about 3:1 to about 2:4, or about 3:1 to about 2:3 including ranges and sub-ranges there between (e.g., about 3:2 to about 2:5, about 2:1 to about 2:5, about 1:1 to about 2:5, about 1:1 to about 2:4, etc.).

In certain embodiments, the cosmetic composition may be formulated to have a weight ratio of the citric acid of (i) to the urea compound of (ii) of about 10:1, 9.5;1, 9:1, 8.5:1, 8:1, 7.5:1, 7:1, 6.5:1, 6;1, 5.5:1, 5:1, 4.5:1, 4:1, 3.5:1, 3:1, 3:2, 2:8:1, 1.4:1, 1.2:1, 1:1, 1:2, 1:3, 1:4, 1:5, 1.6, 1.7, 1.8, or 1.9.

The mole ratio of the citric acid of (i) to the urea compound of (ii) in the compositions of the present disclosure is about 10:0.5 to about 0.5:10, including ranges and sub-ranges there between. In an embodiment, a deep eutectic solvent s formed when the mole ratio of the citric acid of (i) to the urea compound of (ii) is about 10:0.5 to about 0.5:10, including ranges and sub-ranges there between.

For example, the cosmetic composition may be formulated to have a mole or molar ratio of the citric acid of (i) to the urea compound of (ii) of about 10:0.5 to about 0.5:10. In some instances, the cosmetic composition may be formulated to have a weight ratio of citric acid to urea compound(s) of 10:1 to about 0.5:10, about 9:1 to about 0.5:10, about 8:1 to about 0.5:10, about 7:1 to about 0.5:10, about 6:1 to about 0.5:10, about 5:1 to about 0.5:10, about 4:1 to about 0.5:10, about 3:1 to about 0.5:10; 10:1 to about 1:10, about 9:1 to about 1:10, about 8:1 to about 1:10, about 8:1 to about 1:8, about 7:1 to about 1:10, about 6:1 to about 1:10, about 6:1 to about 1:6, about 5:1 to about 1:10, about 4:1 to about 1:10, about 3:1 to about 1:10; about 10:1 to about 2:10, about 9:1 to about 2:10, about 8:1 to about 2:10, about 7:1 to about 2:10, about 6:1 to about 2:10, about 5:1 to about 2:10, about 4:1 to about 2:10, about 3:1 to about 2:10; about 10:1 to about 2:8, about 9:1 to about 2:8, about 8:1 to about 2:8, about 7:1 to about 2:8, about 6:1 to about 2:8, about 5:1 to about 2:8, about 4:1 to about 2:8, about 3:1 to about 2:8; about 10:1 to about 2:6, about 9:1 to about 2:6, about 8:1 to about 2:6, about 7:1 to about 2:6, about 6:1 to about 2:6, about 5:1 to about 2:6, about 5:1 to about 1:2, about 4:1 to about 2:6, about 3:2 to about 2:6; about 2:1 to about 2:10, about 1:1 to about 2:10, about 3:2 to about 2:9, about 3:2 to about 2:8, about 3:2 to about 2:7, about 3:2 to about 2:6, about 3:2 to about 2:5, about 3:2 to about 2:4, about 3:2 to about 2:3, about 3:2 to about 1:3, about 3:1 to about 1:3, about 1:1 to about 1:4, about 1:1 to about 1:3, about 1:1 to about 1:2, or about 1:1.3 to about 1:1.6, including ranges and sub-ranges therebetween (e.g., about 3:1 to about 2:5, about 2.5:1 to about 2:3, about 2:1 to about 2:5, about 1:1 to about 2:5, about 1:1 to about 2:4, etc.).

In certain embodiments, the cosmetic composition may be formulated to have a mole or molar ratio of the citric acid of (i) to the urea compound of (ii) of about 10:1, 9.5:1, 9:1, 8.5:1, 8:1, 7.5:1, 7:1, 6.5:1, 6;1, 5.5:1, 5:1, 4.5:1, 4:1, 3.5:1, 3.3:1, 3:1, 2.5:1, 2:3, 2:1, 1.9:1, 1.8:1, 1:7:1, 1.6:1, 1:5:1, 1.4:1, 1.3:1, 1.2:1, 1.1:1, 1:1, 1:1.2, 1:1.3, 1:1.4, 1:1.5, 1:2, 1:3, 1:4, 1:5, 1:6, 1:7, 1:8, 1:9, 1:10, 1:0.1, 1:0.2, 1:0.3, 1:0.4, 1:0.5, 1:0.6, 1:0.7, 1:0.8, or 1:0.9.

The citric acid and urea, or a portion thereof, may form a deep eutectic solvent system ("DES") system before inclusion into the base composition of the cosmetic composition. The base composition of the cosmetic composition may be a composition of one or more components of the cosmetic composition. For example, in some instances, the base composition may include all components of the cosmetic composition except for the citric acid and urea compound(s). The cosmetic composition may at least partially include the DES system after the DES system is incorporated into the base cosmetic composition. Further description of the DES system and methods for making the DES system is disclosed herein.

During use, a user combines the cosmetic compositions with extraneous water (e.g., water other than the water already included in the cosmetic composition). As the cosmetic composition becomes mixed or placed in contact with extraneous water, the cosmetic composition may form a lamellar phase structure. A "lamellar phase structure" refers generally to packing of polar-headed long chain nonpolar-tail molecules in an environment of bulk polar liquid (i.e., water from the hair), as sheets of bilayers separated by bulk liquid. In some cases, the cosmetic composition may form a mixed structure upon combination with extraneous water. As used herein, the term "mixed structure" refers to a combination of a lamellar phase and crystals. Additionally or alternatively, the cosmetic compositions may form an opaque emulsion or turbid emulsion upon combination with extraneous water.

In some cases, the cosmetic composition forms a lamellar phase structure, mixed structure phase, and/or an opaque emulsion when combining extraneous water with the cosmetic composition in an ratio (water:composition) ranging from 0.1:1 to 3:1, preferably 0.5:1 or 1:1 or 1.5:1 or 2:1. Additionally and/or alternatively, formation of the lamellar phase structure, mixed structure phase, and/or an opaque emulsion may occur by combining extraneous water in an amount such that the total amount of water in the cosmetic composition increases to more than 10 wt. % or, in some instances, to 12 wt. % or more, 15 wt. % or more, 20 wt. % or more, 25 wt. % or more, or 30 wt. % or more, based on the total weight of the cosmetic composition before combination with extraneous water. In some embodiments, the opaque or turbid emulsion has a viscosity that is the same or greater than that of the composition prior to combination with the extraneous water.

The cosmetic composition may form a lamellar phase structure, mixed structure phase, and/or an opaque emulsion upon combination with extraneous water, for example, from a user's wet or damp hands, wet or damp skin, wet or damp hair, and/or from the faucet and the like. This can occur, for example, when a consumer applies the cosmetic composition to a wet or damp part of the body (e.g., hands, face, skin, hair, etc.). The user may then physically manipulate the applied cosmetic composition (for example, by rubbing the hands together or rubbing the composition against another part of the body such as the face, hair, etc.). In some instances, formation of the lamellar phase structure, mixed structure phase, and/or an opaque emulsion occurs automatically without the need for mixing. In other words, the cosmetic composition becomes sufficiently combined with extraneous water by simply coming into contact with extraneous water. In some instances, however, a minimal amount of mixing may be needed, and may be encouraged.

The mixed structure formed from the combination of the cosmetic composition and extraneous water may occur without active mixing from a user or in conjunction with active mixing from the user. For example, this can easily be achieved during use of the cosmetic composition, for example, by physically manipulating (e.g., mixing) the cosmetic composition with extraneous water using the body (e.g., with the hands).

The cosmetic composition is typically translucent or clear before combination with extraneous water. For example, the cosmetic composition may have a transmittance of at least 50% at a wavelength of 600 nm, for example measured using a Lambda 40 UV-visible spectrometer. In some instances, the compositions may have a transmittance of at least 60%, at least 70%, at least 80%, at least 90%, or at least 95% at a wavelength of 600 nm, measured, for example, using a Lambda 40 UV-visible spectrometer.

The cosmetic compositions typically have a viscosity of about 1 Pa·s or less at a shear rate of 1 s$^{-1}$ at a temperature of 25° C. before combination with extraneous water. For example, the cosmetic compositions may have a viscosity of about 1 mPa·s to about 1 Pa·s, about 1 mPa·s to about 800 mPa·s, about 1 mPa·s to about 600 mPa·s, about 1 mPa·s to about 500 mPa·s, about 1 mPa·s to about 400 mPa·s, or about 1 mPa·s to about 300 mPa·s; about 100 mPa·s to about 1 Pa·s, about 100 mPa·s to about 800 mPa·s, about 100 mPa·s to about 600 mPa·s, about 100 mPa·s to about 500 mPa·s, about 100 mPa·s to about 400 mPa·s, or about 100 mPa·s to about 300 mPa·s; about 300 mPa·s to about 1 Pa·s, about 300 mPa·s to about 800 mPa·s, about 300 mPa·s to about 600 mPa·s, or about 300 mPa·s to about 500 mPa·s; about 500 mPa·s to about 1 Pa·s, about 500 mPa·s to about 800 mPa·s, or about 500 mPa·s to about 600 mPa·s, including ranges and subranges therebetween, at a temperature of 25° C. before combination with extraneous water. The viscosity measurements can be carried out, for example, using a Brooksfield viscometer, Model RVT (Brookfield Engineering Laboratories, Inc.) at about 60 revolutions per minute (RPM), at ambient room temperature of about 20 to 25° C.; spindle sizes may be selected in accordance with the standard operating recommendations form the manufacturer, ranging from disk spindle No. 1 to No. 4.

In some instances, the cosmetic composition is free or substantially free of water (anhydrous or substantially anhydrous). Alternatively or additionally, the cosmetic composition may have an amount of water that is less than 6 wt. %, preferably less than 5 wt. %, preferably less than 4 wt. %, preferably less than 3 wt. %, preferably less than 2 wt. %, preferably less than 1 wt. %, and/or less than 0.5 wt. %, based on the total weight of the cosmetic composition. In at least embodiment, the cosmetic composition has substantially/essentially 0 wt. % or 0 wt. % of water, based on the total weight of the cosmetic composition.

Additionally or alternatively, the cosmetic composition may include arginine. In some cases, the arginine is 1-arginine, d-arginine, and/or may be in a racemic mixture.

Suitable components, such as those listed below, may be included or excluded from the formulations for the cosmetic compositions depending on the specific combination of other components, the form of the cosmetic compositions, and/or the use of the formulation (e.g., a lotion, gel, cream, spray, etc.). The cosmetic compositions may be formulated as a hair care composition and/or hair cosmetic composition and/or hair treatment composition and/or skin care composition and/or scalp care composition, e.g., for use on the hair and/or skin.

Polyol(s)

The cosmetic compositions include one or more polyols. The amount of polyol(s) present in the cosmetic composition typically ranges from about 20 wt. % or more, based on the total weight of the cosmetic composition. For example, the amount of polyol(s) in the cosmetic composition may be about 20 to about 87 wt. %, about 20 to about 85 wt. %, about 20 to about 80 wt. %, about 20 to about 75 wt. %, about 20 to about 70 wt. %, about 20 to about 65 wt. %, about 20 to about 60 wt. %, about 20 to about 55 wt. %, about 20 to about 50 wt. %, about 20 to about 45 wt. %, about 20 to about 40 wt. %, about 20 to about 35 wt. %, about 20 to about 30 wt. %; about 30 to about 87 wt. %, about 30 to about 85 wt. %, about 30 to about 80 wt. %, about 30 to about 75 wt. %, about 30 to about 70 wt. %, about 30 to about 65 wt. %, about 30 to about 60 wt. %, about 30 to about 55 wt. %, about 30 to about 50 wt. %, about 30 to about 45 wt. %, about 30 to about 40 wt. %; about 40 to about 87 wt. %, about 40 to about 85 wt. %, about 40 to about 80 wt. %, about 40 to about 75 wt. %, about 40 to about 70 wt. %, about 40 to about 65 wt. %, about 40 to about 60 wt. %, about 40 to about 55 wt. %, about 40 to about 50 wt. %; about 50 to about 87 wt. %, about 50 to about 85 wt. %, about 50 to about 80 wt. %, about 50 to about 75 wt. %, about 50 to about 70 wt. %, about 50 to about 65 wt. %, about 50 to about 60 wt. %; about 60 to about 87 wt. %, about 60 to about 85 wt. %, about 60 to about 80 wt. %, about 60 to about 75 wt. %, about 60 to about 70 wt. %; about 65 to about 87 wt. %, about 65 to about 85 wt. %, about 65 to about 80 wt. %, about 65 to about 75 wt. %; about 70 to about 87 wt. %, about 70 to about 85 wt. %, about 70 to about 75 wt. %, including all ranges and sub-ranges therebetween, based on the total weight of the cosmetic composition.

The term "polyol" should be understood as meaning, within the meaning of the present disclosure, an organic molecule comprising at least two free hydroxyl groups. The polyols of the cosmetic composition may be glycols or compounds with numerous hydroxyl groups. In some cases, the one or more polyols is/are selected from the group consisting of $C_2$-$C_{32}$ polyols. The one or more polyols may be liquid at ambient temperature (25° C.). The one or more polyols may have from 2 to 32 carbon atoms, from 3 to 16 carbon atoms, or from 3 to 12 carbon atoms.

Polyols that may be included in the cosmetic composition, in certain instances, include ethylene glycol, propylene glycol, butylene glycol, hexylene glycol, glycerin, diglycerin, diethylene glycol, and dipropylene glycol, polyethylene glycols, and mixtures thereof. In some cases, the polyol is propylene glycol. In some further cases, the polyol is one or both of propylene glycol and butylene glycol. Additionally, in some cases, the cosmetic composition comprises at least propylene glycol, and optionally one or more polyols other than propylene glycol.

Non-limiting examples of polyols that may, optionally, be included in the cosmetic include and/or may be chosen from alkanediols such as glycerin, 1,2,6-hexanetriol, trimethylolpropane, ethylene glycol, propylene glycol, butylene glycol, pentylene glycol, hexylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, dipropylene glycol mono-iso-propyl ether, sorbitol, sorbitan, triacetin, and a mixture thereof.

The one or more polyols may, optionally, be glycols or glycol ethers such as, e.g., monomethyl, monoethyl and monobutyl ethers of ethylene glycol, propylene glycol or ethers thereof such as, e.g., monomethyl ether of propylene glycol, butylene glycol, hexylene glycol, dipropylene glycol as well as alkyl ethers of diethylene glycol, e.g., monoethyl ether or monobutyl ether of diethylene glycol. In some cases, the one or more polyols may include or are chosen from ethylene glycol, propylene glycol, butylene glycol, hexylene glycol, pentylene glycol, 1,3-propanediol, diethylene glycol, dipropylene glycol, 1,4-butanediol, 1,5-pentanediol, hexane-1,6-diol, glycerin, diglycerin, caprylyl glycol, polyethylene glycols, and a mixture thereof.

Monoalcohol(s)

The cosmetic compositions include monoalcohol(s), such as those having 1 to 10 carbons, preferably, from 2 to 6 carbons. The amount of monoalcohol present in the cosmetic composition may range from about 5 to about 50 wt. %, based on the total weight of the cosmetic composition. For example, the cosmetic composition may have monoalcohol in an amount of about 5 to about 50 wt. %, about 5 to about 45 wt. %, about 5 to about 40 wt. %, about 5 to about 35 wt. %, about 5 to about 30 wt. %, about 5 to about 25 wt. %; about 10 to about 50 wt. %, about 10 to about 45 wt. %, about 10 to about 40 wt. %, about 10 to about 35 wt. %, about 10 to about 30 wt. %, about 10 to about 25 wt. %; about 15 to about 50 wt. %, about 15 to about 45 wt. %, about 15 to about 40 wt. %, about 15 to about 35 wt. %, about 15 to about 30 wt. %, or about 15 to about 25 wt. % including all ranges and sub-ranges therebetween, based on the total weight of the cosmetic composition.

The one or more monoalcohols of the cosmetic composition may be chosen from ethanol, propanol, butanol, pentanol, hexanol, isopropyl alcohol, cyclohexanol, isobutyl alcohol, 2-methyl-2-butanol (2-methylbutan-2-ol), and a mixture thereof. In some instances, the monoalcohols comprise or are chosen from ethanol, propanol, butanol, pentanol, an isomer thereof, or a combination thereof. In further instances, the one or more monoalcohol(s) includes or consists of ethanol.

Cationic Surfactant(s)

The cosmetic composition includes a cationic surfactant(s). The amount of cationic surfactant(s) may be from about 0.1 to about 10 wt. % of the total weight of the cosmetic composition. In some instances, the cationic surfactant(s) are in an amount ranging from about 0.1 to about 10 wt. %, about 0.1 to about 8 wt. %, about 0.1 to about 6 wt. %, about 0.1 to about 4 wt. %, about 0.1 to about 3 wt. %; about 0.2 to about 10 wt. %, about 0.2 to about 8 wt. %, about 0.2 to about 6 wt. %, about 0.2 to about 4 wt. %, about 0.2 to about 3 wt. %; about 0.5 to about 10 wt. %, about 0.5 to about 8 wt. %, about 0.5 to about 6 wt. %, about 0.5 to about 4 wt. %, about 0.5 to about 3 wt. %; about 1 to about 10 wt. %, about 1 to about 8 wt. %, about 1 to about 6 wt. %, about 1 to about 4 wt. %, about 1 to about 3 wt. %; about 1.5 to about 10 wt. %, about 1.5 to about 8 wt. %, about 1.5 to about 6 wt. %, about 1.5 to about 4 wt. %, about 1.5 to about 3 wt. %; about 2 to about 10 wt. %, about 2 to about 8 wt. %, about 2 to about 6 wt. %, about 2 to about 4 wt. %, about 2 to about 3 wt. %, including ranges and sub-ranges therebetween, based on the total weight of the cosmetic composition.

In certain embodiments, the cationic surfactants include or are chosen from cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and mixtures thereof.

Additional, non-limiting examples of cationic surfactants include behenalkonium chloride, benzethonium chloride, cetylpyridinium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, hexadecyltrimethyl ammonium bromide, and mixtures thereof.

The cationic surfactant(s) may also be chosen from optionally polyoxyalkylenated, primary, secondary or tertiary fatty amines, or salts thereof, and quaternary ammonium salts, and mixtures thereof. In some cases it is useful to use salts such as chloride salts of the quaternary ammonium compounds.

The fatty amines generally comprise at least one $C_8$-$C_{30}$ hydrocarbon-based chain. For example, quaternary ammonium salts, which may be incorporated in certain instances, include those corresponding to the following general formula:

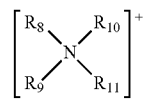

in which the groups $R_8$ to $R_{11}$, which may be identical or different, represent a linear or branched, saturated or unsaturated aliphatic group comprising from 1 to 30 carbon atoms, or an aromatic group such as aryl or alkylaryl, at least one of the groups $R_8$ to $R_{11}$ denoting a group comprising from 8 to 30 carbon atoms and preferably from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_2$-$C_{30}$ alkenyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups; $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Among the quaternary ammonium salts having a structure in accordance with the above general formula (III), those that are preferred are, on the one hand, tetraalkylammonium salts, for instance dialkyldimethylammonium or alkyltrimethylammonium salts in which the alkyl group contains approximately from 12 to 22 carbon atoms, such as behenyltrimethylammonium, distearyldimethylammonium, cetyltrimethylammonium or benzyldimethylstearylammonium salts, or, on the other hand, oleocetyldimethylhydroxyethylammonium salts, palmitylamidopropyltrimethylammonium salts, stearamidopropyltrimethylammonium salts and stearamidopropyldimethylcetearylammonium salts.

Examples of quaternary ammonium salt of imidazoline, which may be incorporated in certain instances, include those having a structure according to the general formula provided below:

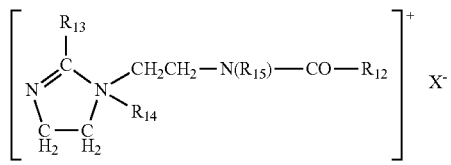

in which $R_{12}$ represents an alkenyl or alkyl group comprising from 8 to 30 carbon atoms, derived for example from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion chosen from the group of halides, phosphates, acetates, lactates, alkyl sulfates, alkyl- or alkylaryl-sulfonates in which the alkyl and aryl groups preferably comprise, respectively, from 1 to 20 carbon atoms and from 6 to 30 carbon atoms. $R_{12}$ and $R_{13}$ preferably denote a mixture of alkenyl or alkyl groups containing from 12 to 21 carbon atoms, derived for example from tallow fatty acids, $R_{14}$ preferably denotes a methyl group, and $R_{15}$ preferably denotes a hydrogen atom. Such a product is sold, for example, under the name REWOQUAT W 75 by the company Rewo.

Examples of quaternary diammonium or triammonium salt, which may be incorporated in certain instances, include those having a structure in accordance with the following general formula:

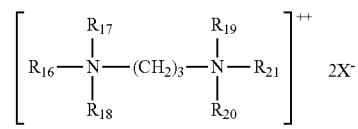

in which $R_{16}$ denotes an alkyl radical comprising approximately from 16 to 30 carbon atoms, which is optionally hydroxylated and/or interrupted with one or more oxygen atoms; $R_{17}$ is chosen from hydrogen or an alkyl radical comprising from 1 to 4 carbon atoms or a group $(R_{16a})(R_{17a})(R_{18a})N$—$(CH_2)_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms; and $X^-$ is an anion chosen from the group of halides, acetates, phosphates, nitrates and methyl sulfates. Such compounds are, for example, Finquat CT-P, sold by the company Finetex (Quaternium 89), and Finquat CT, sold by the company Finetex (Quaternium 75), Examples of cationic/cationizable surfactants, which may be incorporated in certain instances, include those having a structure in accordance with the general formula provided below:

wherein $R_4$ is a saturated or unsaturated, straight or branched alkyl chain with 8 to 24 C atoms, $R_5$ is a straight or branched alkyl chain with 1 to 4 C atoms, A is selected from:

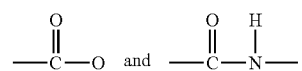

and B is selected from:

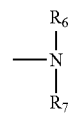

wherein $R_6$ and $R_7$ are the same or different and are H or an alkyl chain with 1 to 4 C atoms, hydroxyl alkyl chain with 1 to 4 C atoms and di hydroxyl alkyl chain with 2 to 4 C atoms,

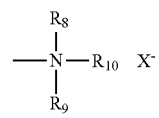

$R_8$ and $R_9$ are the same or different, an alkyl chain with 1 to 4 C atoms, hydroxyl alkyl chain with 1 to 4 C atoms and di hydroxyl alkyl chain with 2 to 4 C atoms, $R_{10}$ is an alkyl chain with 1 to 4 C atoms, hydroxyl alkyl chain with 1 to 4 C atoms or di hydroxyl alkyl chain with 2 to 4 C atoms.

In some instances, $R_4$ is saturated or unsaturated, straight or branched alkyl chain with 10 to 24C atoms, more preferably 12 to 22 C atoms and $R_5$ is straight or branched alkyl group with 1 to 4 C atoms, and A, B, $R_6$ to $R_{10}$ are same as above.

Non-limiting suitable examples are stearyloxypropyl amine, palmityloxypropyl amine, stearyloxypropyldimethyl amine, stearyloxypropyldiethyl amine, stearyloxyethylyldimethyl amine, stearyloxyethyl amine, myristyloxypropyl amine, myristyloxypropyldimethyl amine, palmitamidopropyl amine, palmitamidopropyl methylamine, palmitamidopropyl diethylamine, palmitamidopropyl dibutylamine, palmitamidopropyl buylamine, palmitamidopropyl dipropylamine, palmitamidopropyl propylamine, palmitamidopropyl dihydroxyethylamine, palmitamidopropyl hydroxyethylamine, palmitamidopropyl dihydroxypropylamine, palmitamidopropyl hydroxypropylamine, lauramidopropyl amine, lauramidopropyl methylamine, lauramidopropyl diethylamine, lauramidopropyl dibutylamine, lauramidopropyl buylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearamidopropyl dimethylamine, steara midopropyl diethylamine, stearamidopropyldibutylamine, stearamidopropyl butylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibehenamidopropyl propylamine, dibehenamidopropyl hydroxyethylamine, palmitoamidopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palmitoylpropyl amine, palmitoylpropyl methylamine, palmitoylpropyl diethylamine, palmitoylpropyl dibutylamine, palmitoylpropyl buylamine, palmitoylpropyl dipropylamine, palmitoylpropyl propylamine, palmitoylpropyl dihydroxyethylamine, palmitoylpropyl hydroxyethylamine, palmitoylpropyl dihydroxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, behenylpropyl amine, behenylpropyl methylamine, behenylpropyl diethylamine, behenylpropyl dibutylamine, behenylpropyl butylamine, behenylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, dibehenylpropyl hydroxyethylamine, palmitylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulfate, and dicocoylethylhydroxyethylmonium methosulfate.

Cationizable surfactants may be chosen from fatty alkylamines, preferably, fatty dialkylamines. Non-limiting examples include dimethyl lauramine, dimethyl behenamine, dimethyl cocamine, dimethyl myristamine, dimethyl palmitamine, dimethyl stearamine, dimethyl tallowamine, dimethyl soyamine, and mixtures thereof.

Fatty dialkylamines include fatty amidoamine compounds, their salts, and mixtures thereof. Non-limiting examples include oleamidopropyl dimethylamine, linoleamidopropyl dimethylamine, isostearamidopropyl dimethylamine, stearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, and palmitamidopropyl dimethylamine.

Non-polymeric, mono-, di-, and/or tri-carboxylic acids may be used to "neutralize" the fatty dialkylamines. In some cases, the one or more non-polymeric, mono-, di-, and/or tri-carboxylic acids include at least one dicarboxylic acid. Non-limiting examples include lactic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, benzoic acid, and mixtures thereof. In particular, lactic acid or tartaric acid or mixtures thereofare useful, especially in combination with fatty dimethylamines such as, for example, stearamidopropyl dimethylamine.

In an embodiment, cosmetic composition may be formulated with a cationic surfactant chosen from behentrimonium chloride, cetrimonium chloride, behentrimonium methosulfate, or mixtures thereof.

The cosmetic composition may be formulated such that the two or more cationic surfactants are associated with the same or different balancing anionic ions. For example, at least one of the two or more cationic surfactants may have a chloride ion and/or a sulfate ion. In some instances, the two or more cationic surfactants comprise cetrimonium chloride and one or both of behentrimonium methosulfate and behentrimonium chloride. In further instances, the two or more cationic surfactants comprise behentrimonium chloride and one or both of behentrimonium methosulfate and cetrimonium chloride.

In yet another instance, the cationic surfactant(s) is chosen from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, stearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and a mixture thereof.

Fatty Compound(s)

The cosmetic compositions include one or more fatty compound(s) in amount that may vary, but is typically about 0.1 to about 20 wt. %, based on the total weight of the cosmetic compositions. In some instances, the amount of fatty compounds present in the cosmetic compositions is about 0.1 to 20 wt. %, about 0.1 to about 18 wt. %, about 0.1 to about 16 wt. %, about 0.1 to about 14 wt. %, about 0.1 to about 12 wt. %, about 0.1 to about 10 wt. %, about 0.1 to about 8 wt. %, about 0.1 to about 7 wt. %, about 0.1 to about 6 wt. %, about 0.1 to about 5 wt. %; about 0.5 to 20 wt. %, about 0.5 to about 18 wt. %, about 0.5 to about 16 wt. %, about 0.5 to about 14 wt. %, about 0.5 to about 12 wt. %, about 0.5 to about 10 wt. %, about 0.5 to about 8 wt. %, about 0.5 to about 7 wt. %, about 0.5 to about 6 wt. %, about 0.5 to about 5 wt. %; about 1 to about 20 wt. %, about 1 to about 18 wt. %, about 1 to about 16 wt. %, about 1 to about 14 wt. %, about 1 to about 12 wt. %, about 1 to about 10 wt. %, about 1 to about 8 wt. %, about 1 to about 7 wt. %, about 1 to about 6 wt. %, about 1 to about 5 wt. %; about 2 to about 20 wt. %, about 2 to about 18 wt. %, about 2 to about 16 wt. %, about 2 to about 14 wt. %, about 2 to about 12 wt. %, about 2 to about 10 wt. %, about 2 to about 8 wt. %, about 2 to about 7 wt. %, about 2 to about 6 wt. %, about 2 to about 5 wt. %; about 3 to about 20 wt. %, about 3 to about 18 wt. %, about 3 to about 16 wt. %, about 3 to about 14 wt. %, about 3 to about 12 wt. %, about 3 to about 10 wt. %, about 3 to about 8 wt. %, about 3 to about 7 wt. %, about 3 to about 6 wt. %, about 3 to about 5 wt. %; about 4 to about 20 wt. %, about 4 to about 18 wt. %, about 4 to about 16 wt. %, about 4 to about 14 wt. %, about 4 to about 12 wt. %, about 4 to about 10 wt. %, about 4 to about 8 wt. % about 4 to about 7 wt. %, about 4 to about 6 wt. %, about 4 to about 5 wt. %; about 5 to about 20 wt. %, about 5 to about 18 wt. %, about 5 to about 16 wt. %, about 5 to about 14 wt. %, about 5 to about 12 wt. %, about 5 to about 10 wt. %, or about 5 to about 8 wt. %, about 5 to about 7 wt. %, or about 5 to about 6 wt. %, including all ranges and sub-ranges therebetween, based on the total weight of the cosmetic composition.

Examples of fatty compound(s) that may be incorporated into the cosmetic composition include fatty alcohol, a fatty ester, a fatty ether, a fatty acid, a wax, an oil, a derivative thereof, and a mixture thereof. Additional examples of fatty compounds that are worth mentioning include oils, mineral oil, alkanes (paraffins), fatty alcohol derivatives, fatty acid derivatives, esters of fatty alcohols, hydroxy-substituted fatty acids, waxes, triglyceride compounds, lanolin, and a mixture thereof.

Fatty Ester(s)

The cosmetic compositions may include one or more fatty compound(s) that is a fatty ester. For example, the fatty compound(s) may be chosen from dialkyl carbonates of formula: $R_1O(C=O)R_2$, wherein $R_1$ and $R_2$ are independently linear or branched, saturated or unsaturated alkyl chains having 1 to 30 carbon atoms, or having 2 to 28 carbon atoms, or having 4 to 25 carbon atoms, or having 6 to 22 carbon atoms, preferably one or more fatty carbonates selected from C14-15 dialkyl carbonate, dicaprylyl carbonate, diethyl carbonate, dihexyl carbonate, diethylhexyl carbonate, dimethoxyphenyl phenyloxoethyl ethylcarbonate, dimethyl carbonate, dipropyl carbonate, dipropylheptyl carbonate, dioctyl carbonate, and a mixture thereof.

Additionally or alternatively, the fatty ester chosen from cetyl ester, purcellin oil (cetearyl octanoate), isopropyl myristate, isopropyl palmitate, $C_{12}$-$C_{15}$ alkyl benzoate, 2-ethylphenyl benzoate, isopropyl lanolate, hexyl laurate, diisopropyl adipate, isononyl isononanoate, oleyl erucate, 2-ethylhexyl palmitate, isostearyl isostearate, diisopropyl sebacate, octanoates, decanoates or ricinoleates of alcohols or polyalcohols, hydroxylated esters, dicaprylyl carbonate, pentaerythritol esters, diisostearyl malate, neopentyl glycol dioctanoate, dibutyl sebacate, di-$C_{12-13}$ alkyl malate, dicetearyl dimer dilinoleate, dicetyl adipate, diisocetyl adipate, diisononyl adipate, diisostearyl dimer dilinoleate, diisostearyl fumarate, and a mixture thereof. Other fatty esters worth mentioning include polyglyceryl-10 oleate, polyglyceryl-10 dioleate, polyglyceryl-6 stearate, polyglyceryl-6 distearate, polyglyceryl-10 stearate, polyglyceryl-10 distearate, polyglyceryl-8 dipalmitate, polyglyceryl-10 dipalmitate, polyglyceryl-10 behenate, and polyglyceryl-12 trilaurate.

Fatty Alcohol(s)

Suitable fatty alcohols, if present, include those having a fatty group with a carbon chain of greater than 8 carbon atoms, 8 to 50 carbon atoms, 8 to 40 carbon atoms, 8 to 30 carbon atoms, 8 to 22 carbon atoms, 12 to 22 carbon atoms, or 12 to 18 carbon atoms, including all ranges and subranges therebetween. In some instances, the fatty group of the fatty alcohols has a carbon chain of 10 to 20 carbon atoms or 10 to 18 carbon atoms. The fatty alcohols may be chosen from polyethylene glycol ethers, such as those having a fatty alcohol group with a carbon chain of 12 to 16 or 12 to 14 carbon atoms.

The fatty alcohol portion is preferably hydrogenated (for example, stearyl, lauryl, cetyl, cetearyl); however, the fatty alcohol may contain one or more double bonds (for example, oleyl). Non-limiting examples of fatty alcohols include decyl alcohol, undecyl alcohol, dodecyl alcohol, myristyl alcohol, lauryl alcohol, cetyl alcohol, stearyl alcohol, cetearyl alcohol (cetyl alcohol and stearyl alcohol), isostearyl alcohol, isocetyl alcohol, behenyl alcohol, linalool, oleyl alcohol, cis-4-t-butylcyclohexanol, isotridecyl alcohol, myricyl alcohol, and a mixture thereof. In some cases, the fatty alcohols comprise at least one of or may be chosen from myristyl alcohol, lauryl alcohol, cetyl alcohol, stearyl alcohol, cetearyl alcohol, isostearyl alcohol, oleyl alcohol, isotridecyl alcohol, and a mixture thereof.

The fatty alcohol may be saturated or unsaturated. Exemplary saturated liquid fatty alcohols may be branched and optionally contain in their structure at least one aromatic or non-aromatic ring. In some instances, however, the fatty alcohols are acyclic. Non-limiting examples of liquid saturated fatty alcohols include octyldodecanol, isostearyl alcohol, and 2-hexyldecanol.

Exemplary unsaturated liquid fatty alcohol may include in their structure at least one double or triple bond. For example, the fatty alcohols may include several double bonds (such as 2 or 3 double bond), which may be conjugated or non-conjugated. The unsaturated fatty alcohols can be linear or branched and may be acyclic or include in their structure at least one aromatic or non-aromatic ring. Liquid unsaturated fatty alcohols may include or be chosen from oleyl alcohol, linoleyl alcohol, linolenyl alcohol and undecylenyl alcohol.

The fatty alcohols may be alkoxylated fatty alcohols, e.g., having about 1 to about 100 moles of an alkylene oxide per mole of alkoxylated fatty alcohol. For example, the alkoxylated fatty alcohols may be alkoxylated with about 1 to about 80 moles, about 2 to about 50, about 5 to about 45 moles, about 10 to about 40 moles, or 15 to about 35 mores, including all ranges and subranges therebetween, of an alkylene oxide per mole of alkoxylated fatty alcohol.

As examples of alkoxylated fatty alcohols, steareth (for example, steareth-2, steareth-20, and steareth-21), laureth (for example, laureth-4, and laureth-12), ceteth (for example, ceteth-10 and ceteth-20) and ceteareth (for example, ceteareth-2, ceteareth-10, and ceteareth-20) are mentioned. In at least one instance, the one or more alkoxylated fatty alcohols include steareth-20. In some instances, the one or more alkoxylated fatty alcohols may be exclusively steareth-20.

Additional fatty alcohol derivatives that may, optionally be suitable include methyl stearyl ether; 2-ethylhexyl dodecyl ether; stearyl acetate; cetyl propionate; the ceteth series of compounds, such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Fatty Ether(s)

The fatty compounds may be chosen from fatty ethers. For example, the cosmetic composition may include olyoxyethylene cetyl/stearyl ether, polyoxyethylene cholesterol ether, polyoxyethylene laurate or dilaurate, polyoxyethylene stearate or distearate, polyoxyethylene lauryl or stearyl ether, dicaprylyl ether, dicetyl ether distearyl ether, dodecyl ether, dilauryl ether, dimyristyl ether, diisononyl ether, or a mixture thereof. Non-limiting examples of suitable polyoxyethylene fatty ethers include, but are not limited to, polyoxyethylene cetyl/stearyl ether, polyoxyethylene cholesterol ether, polyoxyethylene laurate or dilaurate, polyoxyethylene stearate or distearate, polyoxyethylene lauryl or stearyl ether, and mixtures thereof, wherein the polyoxyethylene head group ranges from about 2 to about 100 groups.

In certain embodiments, the polyoxyethylene fatty ethers include polyoxyethylene stearyl ether, polyoxyethylene myristyl ether, polyoxyethylene lauryl ether having from about 3 to about 10 oxyethylene units and mixtures thereof.

Fatty Acid(s)

In some instances, the fatty compounds may be chosen from fatty acids, fatty acid derivatives, esters of fatty acids, hydroxyl-substituted fatty acids, and alkoxylated fatty acids. The fatty acids may be straight or branched chain acids and/or may be saturated or unsaturated. Non-limiting examples of fatty acids include diacids, triacids, and other multiple acids as well as salts of these fatty acids. For example, the fatty acid may optionally include or be chosen from lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Non-limiting examples of polyglycerol esters of fatty acids include those of the following formula:

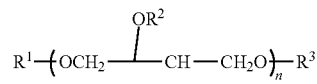

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Non-limiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

Wax(es)

The fatty compounds may, in some instances, include or be chosen from one or more waxes. Non-limiting examples of waxes in this category include for example, synthetic wax, ceresin, paraffin, ozokerite, polyethylene waxes, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, acacia decurrents flower wax, vegetable waxes (such as sunflower seed (*Elianthus annuus*), carnauba, candelilla, ouricury or japan wax or cork fibre or sugarcane waxes), or a mixture thereof.

Oil(s)

In some instances, the fatty compounds may include or be chosen from one or more oil(s). Suitable oils include, but are not limited to, synthetic oils such as silicone oils; natural oils, such as coconut oil; hydrocarbons, such as mineral oil and hydrogenated polyisobutene; fatty alcohols, such as octyldodecanol; esters, such as $C_{12}$-$C_{15}$ alkyl benzoate; diesters, such as propylene dipelarganate; and triesters, such as glyceryl trioctanoate. Non-limiting examples of oils that may, optionally, be included in the cosmetic compositions include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isodecanol, polyglyceryl-3-diisostearate, castor oil, lanolin and lanolin derivatives, triisocetyl citrate, sorbitan sesquioleate, $C_{10}$-$C_{18}$ triglycerides, caprylic/capric/triglycerides, coconut oil, corn oil, cottonseed oil, glyceryl tri acetyl hydroxystearate, glyceryl tri acetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof.

Combination of Urea Compound(s) and Citric Acid

The combination of the citric acid and the urea compound(s) is typically presented in the cosmetic composition in an amount of about 1 to about 15 wt. %, based on the total weight of the cosmetic composition. In some cases, the combination of the citric acid and the urea compound(s) is present in an amount of about 1 to about 15 wt. %, about 1 to about 15 wt. %, about 1 to about 13 wt. %, about 1 to about 11 wt. %, about 1 to about 10 wt. %, about 1 to about 15 wt. %, about 1 to about 9 wt. %, about 1 to about 8 wt. %, about 1 to about 7 wt. %, about 1 to about 6 wt. %, about 1 to about 5 wt. %, about 1 to about 4 wt. %; about 1.5 to about 15 wt. %, about 1.5 to about 15 wt. %, about 1.5 to about 13 wt. %, about 1.5 to about 11 wt. %, about 1.5 to about 10 wt. %, about 1.5 to about 15 wt. %, about 1.5 to about 9 wt. %, about 1.5 to about 8 wt. %, about 1.5 to about 7 wt. %, about 1.5 to about 6 wt. %, about 1.5 to about 5 wt. %, about 1.5 to about 4 wt. %; about 2 to about 15 wt. %, about 2 to about 15 wt. %, about 2 to about 13 wt. %, about 2 to about 11 wt. %, about 2 to about 10 wt. %, about 2 to about 15 wt. %, about 2 to about 9 wt. %, about 2 to about 8 wt. %, about 2 to about 7 wt. %, about 2 to about 6 wt. %, about 2 to about 5 wt. %; about 3 to about 15 wt. %, about 3 to about 15 wt. %, about 3 to about 13 wt. %, about 3 to about 11 wt. %, about 3 to about 10 wt. %, about 3 to about 15 wt. %, about 3 to about 9 wt. %, about 3 to about 8 wt. %, about 3 to about 7 wt. %, about 3 to about 6 wt. %, about 3 to about 5 wt. %; about 4 to about 15 wt. %, about 4 to about 15 wt. %, about 4 to about 13 wt. %, about 4 to about 11 wt. %, about 4 to about 10 wt. %, about 4 to about 15 wt. %, about 4 to about 9 wt. %, about 4 to about 8 wt. %, about 4 to about 7 wt. %, or about 4 to about 6, including ranges and subranges thereof, based on the total weight of the cosmetic composition.

The combination of the citric acid and the urea compound(s) are typically prepared as pre-phase component. In other words, the combination of citric acid and urea compounds is typically produced, e.g., by combining/mixing the citric acid and urea compounds, before the combination is added to the base composition of the cosmetic composition.

The combination of the citric acid and the urea compound may or may not be in the form of a deep eutectic solvent system ("DES") system. Preferably, the cosmetic composition at least partially includes a DES system. The cosmetic compositions may include an amount of DES system of about 1 wt. % or more, based on the total weight of the cosmetic composition. In some cases, the amount of the deep eutectic solvent is about 1 wt. % or more, preferably about 2 wt. % or more, about 3 wt. % or more, about 4 wt. % or more, about 5 wt. % or more, about 6 wt. % or more, about 7 wt. % or more, about 8 wt. % or more, about 9 wt. % or more, about 10 wt. % or more, about 12 wt. % or more, or about 14 wt. % or more, based on the total weight of the cosmetic composition. Additionally or alternatively, the combination of the citric acid and the urea compound(s) is in the form of a DES system before inclusion into the base of the cosmetic composition.

The DES system may comprise the citric acid and the urea compounds. In some cases, the DES system is formed from citric acid and one or more urea compound, such as those chosen from dimethyl urea, a hydroxyl ethyl urea, urea, and a mixture thereof.

The combination of the citric acid and the urea compound(s) may comprise an amount of citric acid of about 0.5 to about 12 wt. %, about 0.5 to about 10 wt. %, about 0.5 to about 8 wt. %, about 0.5 to about 6 wt. %, about 0.5 to about 4 wt. %, about 0.5 to about 3 wt. %; about 1 to about 12 wt. %, about 1 to about 10 wt. %, about 1 to about 8 wt. %, about 1 to about 6 wt. %, about 1 to about 4 wt. %, about 1 to about 3 wt. %; about 1.5 to about 12 wt. %, about 1.5 to about 10 wt. %, about 1.5 to about 8 wt. %, about 1.5 to about 6 wt. %, about 1.5 to about 4 wt. %, about 1.5 to about 3 wt. %; about 2 to about 12 wt. %, about 2 to about 10 wt. %, about 2 to about 8 wt. %, about 2 to about 6 wt. %, about 2 to about 4 wt. %, about 2 to about 3 wt. %; about 3 to about 12 wt. %, about 3 to about 10 wt. %, about 3 to about 8 wt. %, about 3 to about 6 wt. %, about 3 to about 4 wt. %; about 4 to about 12 wt. %, about 4 to about 10 wt. %, about 4 to about 8 wt. %, about 4 to about 6 wt. %; about 5 to about 12 wt. %, about 5 to about 10 wt. %, about 5 to about 8 wt. %, about 5 to about 6 wt. %; about 6 to about 12 wt. %, about 6 to about 10 wt. %, about 6 to about 8 wt. %; about 7 to about 12 wt. %, about 7 to about 10 wt. %, about 7 to about 8 wt. %; about 8 to about 12 wt. %, about 8 to about 11 wt. %, about 8 to about 10 wt. %; about 9 to about 12 wt. %, about 9 to about 11 wt. %, about 9 to about 10 wt. %; about 10 to about 12 wt. %, or about 10 to about 11 wt. %, including ranges and sub-ranges therebetween, based on the total weight of the cosmetic composition.

The combination of the citric acid and the urea compound(s) may comprise an amount of urea compounds of about 0.5 to about 12 wt. %, about 1 to about 10 wt. %, about 1 to about 8 wt. %, about 1 to about 6 wt. %, about 1 to about 4 wt. %, about 1 to about 3 wt. %; about 1.5 to about 12 wt. %, about 1.5 to about 10 wt. %, about 1.5 to about 8 wt. %, about 1.5 to about 6 wt. %, about 1.5 to about 4 wt. %, about 1.5 to about 3 wt. %; about 2 to about 12 wt. %, about 2 to about 10 wt. %, about 2 to about 8 wt. %, about 2 to about 6 wt. %, about 2 to about 4 wt. %, about 2 to about 3 wt. %; about 3 to about 12 wt. %, about 3 to about 10 wt. %, about 3 to about 8 wt. %, about 3 to about 6 wt. %, about 3 to about 4 wt. %; about 4 to about 12 wt. %, about 4 to about 10 wt. %, about 4 to about 8 wt. %, about 4 to about 6 wt. %; about 5 to about 12 wt. %, about 5 to about 10 wt. %, about 5 to about 8 wt. %, about 5 to about 6 wt. %; about 6 to about 12 wt. %, about 6 to about 10 wt. %, about 6 to about 8 wt. %; about 7 to about 12 wt. %, about 7 to about 10 wt. %, about 7 to about 8 wt. %; about 8 to about 12 wt. %, about 8 to about 11 wt. %, about 8 to about 10 wt. %; about 9 to about 12 wt. %, about 9 to about 11 wt. %, about 9 to about 10 wt. %; about 10 to about 12 wt. %, or about 10 to about 11 wt. %, including ranges and sub-ranges therebetween, based on the total weight of the cosmetic composition.

The urea compounds may have a structure in accordance with the following formula:

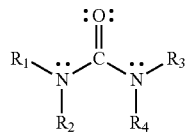

wherein $R_1$, $R_2$, $R_3$, and $R_4$ are independently selected from hydrogens, $C_4$ to $C_{10}$ unsubstituted aryl, $C_4$ to $C_{10}$ substituted aryl, $C_2$ to $C_{10}$ unsubstituted heterocycle, $C_2$ to $C_{10}$ substituted heterocycle, $C_1$ to $C_{10}$ unsubstituted alkyl, $C_1$ to $C_{10}$ substituted alkyl, $C_3$-$C_{10}$ unsubstituted cycloalkyl, and $C_3$-$C_{10}$ substituted cycloalkyl.

The urea compounds are preferably chosen from is dimethyl urea, a hydroxyethyl urea, urea or mixtures thereof. Non-limiting examples of urea compounds include imidazolidinyl urea, diazolidinyl urea, m-dimethylaminophenyl urea, dimethyl urea, a hydroxyethyl urea, urea, urea derivatives, imidazolidinyl urea, diazolidinyl urea, m-dimethylaminophenyl urea, dimethyl urea, a hydroxyethyl urea, N-(2-hydroxyethyl)urea; N-(2-hydroxypropyl)urea; N-(3-hydroxypropyl)urea; N-(2,3-dihydroxypropyl)urea; N-(2,3,4,5,6-pentahydroxyhexyl)urea; N-methyl-N-(1,3,4,5,6-pentahydroxy-2-hexyl)urea; N-methyl-N'-(1-hydroxy-2-methyl-2-propyl)urea; N-(1-hydroxy-2-methyl-2-propyl)urea; N-(1,3-dihydroxy-2-propyl)urea; N-(tris-hydroxymethylmethyl)urea; N-ethyl-N'-(2-hydroxyethyl)urea; N,N-bis(2-hydroxyethyl)urea; N,N'-bis(2-hydroxyethyl)urea; N,N-bis(2-hydroxypropyl)urea; N,N'-bis(2-hydroxypropyl)urea; N,N-bis(2-hydroxyethyl)-N'-propylurea; N,N-bis(2-hydroxypropyl)-N'-(2-hydroxyethyl)urea; N-tert-butyl-N'-(2-hydroxyethyl)-N'-(2-hydroxypropyl)urea; N-(1,3-dihydroxy-2-propyl)-N'-(2-hydroxyethyl)urea; N,N-bis(2-hydroxyethyl).-N',N'-dimethylurea; N,N,N',N'-tetrakis(2-hydroxyethyl)urea; N',N'-bis(2-hydroxyethyl)-N', and/or N'-bis(2-hydroxypropyl)-urea.

Thickening Agent(s)

The cosmetic compositions described herein may, optionally, include a thickening agent. The amount of thickening agents can vary but is typically from about 0.01 to about 20 wt. %, based on the total weight of the cosmetic composition. In some instances, the total amount of thickening agents is about 0.01 to about 15 wt. %, about 0.01 to about 10 wt. %, about 0.01 to about 0.01 to about 8 wt. %, about 0.01 to about 6 wt. %, about 0.01 to about 5 wt. %, about 0.1 to about 20 wt. %, about 0.1 to about 15 wt. %, about 0.1 to about 10 wt. %, about 0.1 to about 8 wt. %, about 0.1 to about 6 wt. %, or about 0.1 to about 5 wt. %, including ranges and sub-ranges therebetween, based on the total weight of the cosmetic composition.

The thickening agent(s) may be chosen from xanthan gum, guar gum, biosaccharide gum, cellulose, acacia seneca gum, sclerotium gum, agarose, pechtin, gellan gum, hyaluronic acid. Additionally, the one or more thickening agents may include polymeric thickening agents selected from the group consisting of ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer. In some cases, the composition includes ammonium polyacryloyldimethyl taurate and/or sodium polyacrylate. Suitable thickening agents may be found in U.S. patent application Ser. No. 16/731,654, which is incorporated herein, in its entirety for all purposes.

Many thickening agents are water-soluble, and increase the viscosity of water or form an aqueous gel when the cosmetic composition of the invention is dispersed/dissolved in water. The aqueous solution may be heated and cooled, or neutralized, for forming the gel, if necessary. The thickener may be dispersed/dissolved in an aqueous solvent that is soluble in water, e.g., ethyl alcohol when it is dispersed/dissolved in water.

Particular types of thickening agents that may be mentioned include the following:

One or more thickening agents can optionally be included in the cosmetic compositions of the instant disclosure. Thickening agents may be referred to as "thickeners" or "viscosity modifying agents." Thickening agents are typically included to increase the viscosity of the cosmetic compositions. Nonetheless, in some instances, certain thickening agents provide additional, surprising benefits to the cosmetic compositions. Non-limiting examples of thickening agents include polyacrylate crosspolymers or crosslinked polyacrylate polymers, cationic acrylate copolymers, anionic acrylic or carboxylic acid polymers, polyacrylamide polymers, polysaccharides such as cellulose derivatives, gums, polyquaterniums, vinylpyrrolidone homopolymers/copolymers, C8-24 hydroxyl substituted aliphatic acid, C8-24 conjugated aliphatic acid, sugar fatty esters, polyglyceryl esters, and a mixture thereof. Particular types of thickening agents that may be mentioned include the following:

Carboxylic Acid or Carboxylate Based Homopolymer or Co-Polymer, which can be Linear or Crosslinked:

These polymers contain one or more monomers derived from acrylic acid, substituted acrylic acids, and salts and esters of these acrylic acids (acrylates) and the substituted acrylic acids. Commercially available polymers include those sold under the trade names CARBOPOL, ACRYSOL, POLYGEL, SOKALAN, CARBOPOL ULTREZ, and POLYGEL. Examples of commercially available carboxylic acid polymers include the carbomers, which are homopolymers of acrylic acid crosslinked with allyl ethers of sucrose or pentaerytritol. The carbomers are available as the CARBOPOL 900 series from B.F. Goodrich (e.g., CARBOPOL 954). In addition, other suitable carboxylic acid polymeric agents include ULTREZ 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as CARBOPOL 1342, CARBOPOL 1382, PEMULEN TR-1, and PEMULEN TR-2, from B.F. Goodrich.

Other suitable carboxylic acid or carboxylate polymeric agents include copolymers of acrylic acid and alkyl C5-C10 acrylate, copolymers of acrylic acid and maleic anhydride, and polyacrylate crosspolymer-6. Polyacrylate Crosspolymer-6 is aviable in the raw material known as SEPIMAX ZEN from Seppic.

Another suitable carboxylic acid or carboxylate polymeric agent includes acrylamidopropyltrimonium chloride/acrylates copolymer, a cationic acrylates copolymer (or a quaternary ammonium compound), available as a raw material known under the tradename of SIMULQUAT HC 305 from Seppic.

In certain embodiments, the carboxylic acid or carboxylate polymer thickening agents useful herein are those selected from carbomers, acrylates/C10-C30 alkyl acrylate crosspolymers, polyacrylate crosspolymer-6, acrylamidopropyltrimonium chloride/acrylates copolymer, and mixtures thereof.

Polyquaternium Compounds:

Non-limiting examples, include polyquaternium-1, polyquaternium-2, polyquaternium-3, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-21, polyquaternium-22, polyquaternium-23, polyquaternium-24, polyquaternium-25, polyquaternium-26, polyquaternium-27, polyquaternium-28, polyquaternium-29, polyquaternium-30, polyquaternium-40, polyquaternium-41, polyquaternium-42, polyquaternium-43, polyquaternium-44, polyquaternium-45, polyquaternium-46, polyquaternium-47, polyquaternium-48, polyquaternium-49, polyquaternium-50, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-61, polyquaternium-62, polyquaternium-63, polyquaternium-64, polyquaternium-65, polyquaternium-66, polyquaternium-67, etc. In some cases, preferred polyquaternium compounds include polyquaternium-10, polyquaternium-11, polyquaternium-67, and a mixture thereof.

Celluloses:

Non-limiting examples of celluloses include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. In some instances, the cellulose is selected from water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt). Furthermore, in some instance, the cellulose is preferably hydroxypropylcellulose (HPC).

Polyvinylpyrrolidone (PVP) and Co-Polymers:

Non-limiting examples include Polyvinylpyrrolidone (PVP), Polyvinylpyrrolidone (PVP)/vinyl acetate copolymer (PVP/VA copolymer), polyvinylpyrrolidone (PVP)/eicosene copolymer, PVP/hexadecene copolymer, etc. Commercially available polyvinylpyrrolidone includes LUVISKOL K30, K85, K90 available from BASF. Commerically available copolymers of vinylpyrrolidone and vinylacetate include LUVISKOL VA37, VA64 available from BASF; copolymers of vinylpyrrolidone, methacrylamide, and vinylimidazole (INCI: VP/Methacrylamide/Vinyl Imidazole Copolymer) is commercially available as LUVISET from BASF. In some instances, PVP and PVP/VA copolymer are preferred.

Sucrose Esters:

Non-limiting examples include sucrose palmitate, sucrose cocoate, sucrose monooctanoate, sucrose monodecanoate, sucrose mono- or dilaurate, sucrose monomyristate, sucrose mono- or dipalmitate, sucrose mono- and distearate, sucrose mono-, di- or trioleate, sucrose mono- or dilinoleate, sucrose pentaoleate, sucrose hexaoleate, sucrose heptaoleate or sucrose octooleate, and mixed esters, such as sucrose palmitate/stearate, and mixtures thereof.

Polyglyceryl Esters:

Non-limiting polyglycerol esters of fatty acids (polygylceryl esters) include those of the following formula:

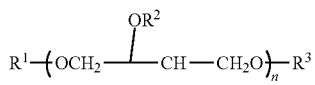

wherein n is from 2 to 20 or from 2 to 10 or from 2 to 5, or is 2, 3, 4, 5, 6, 7, 8, 9, or 10, and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and mixtures thereof.

Gums:

Non-limiting examples of gums include gum arabic, tragacanth gum, karaya gum, guar gum, gellan gum, tara gum, locust bean gum, tamarind gum, xanthan gum, locust bean gum, seneca gum, sclerotium gum, gellan gum, etc.

pH Adjuster(s)

The cosmetic composition may include one or more pH adjusters to increase or decrease the overall pH of the cosmetic composition. For example, one or more acids may be included to decrease the pH of the cosmetic composition. Examples of suitable acids for decreasing the pH of the cosmetic composition include, but are not limited to, citric acid, acetic acid, and the like. The cosmetic composition may include one or more bases, such as sodium hydroxide, potassium hydroxide and the like, to increase the pH of the cosmetic composition. Additional or alternative acids and bases that are suitable for adjusting the pH of the cosmetic composition are readily known to one of ordinary skill in the art.

The amount of the pH adjuster in the cosmetic composition may be based on the desired pH of the final cosmetic composition and/or product. For example, the total amount of the pH adjuster may range from about 0.05 to about 20 wt. %, based on the total weight of the cosmetic composition. In some instances, the total amount of pH adjuster is from about 0.05 to about 15 wt. %, about 0.1 to about 10 wt. %, or about 0.12 to about 5 wt. %, including ranges and sub-ranges therebetween, based on the total weight of the cosmetic composition.

Water

The cosmetic composition may optionally include 10 wt. % or less of water. For example, the amount of water present in the cosmetic composition prior to combination with extraneous water may be 10 wt. % or less, 9 wt. % or less, 8 wt. % or less, 7 wt. % or less, 6 wt. % or less, 5 wt. % or less, 4 wt. % or less, 3 wt. % or less, 2 wt. % or less, 1 wt. % or less, or 0.5 wt. % or less, based on the total weight of the cosmetic composition. In some instances, the water present in the cosmetic composition prior to combination with extraneous water is added to the composition ("added water"). In some instances, the water present in the cosmetic composition prior to combination with extraneous water is not "added water," i.e., it is present in the cosmetic composition as part of a raw material that is included in the cosmetic composition. Although the cosmetic composition may include water prior to the combination of extraneous water, in some embodiments the cosmetic composition is free of water or substantially free of water.

Ester(s)

The cosmetic compositions may optionally include esters, such as ester oils chosen from one or more diester, one or more triglycerides, and mixtures thereof. The amount of diesters present in the cosmetic composition may range from, e.g., about 0.05 to about 4.5 wt. %, about 0.1 to about 4 wt. %, about 0.1 to about 3.5 wt. %, about 0.1 to about 3 wt. %, about 0.5 to about 3 wt. %, about 0.5 to about 2.5 wt. %; about 0.5 to about 2 wt. %, or about 0.5 to about 1.5 wt. %, including all ranges and sub-ranges therebetween, based on the total weight of the cosmetic composition. In certain embodiments, the amount of diesters present in the cosmetic composition is about 0.05. 0.1, 0.15, 0.2, 0.25, 0.3, 0.35, 0.4, 0.45, 0.5, 0.75, 1, 1.25, 1.5, 1.75, 2, 2.25, 2.5, 2.75, 3 wt. %, based on the total weight of the cosmetic composition.

Non-limiting examples of liquid esters include fatty esters from a $C_6$-$C_{32}$ fatty acid and/or a $C_6$-$C_{32}$ fatty alcohol, and are liquid at 25° C., 1 atm. These esters may be liquid esters of saturated or unsaturated, linear or branched $C_1$-$C_{26}$ aliphatic mono or polyacids and of saturated or unsaturated, linear or branched $C_1$-$C_{26}$ aliphatic mono or polyalcohols, the total number of carbon atoms in the esters being greater than or equal to 10. In some cases, for the esters of monoalcohols, at least one of the alcohol or the acid from which the esters of the invention result is branched. Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isononyl isononanoate, isodecyl neopentanoate and isostearyl neopentanoate.

In some cases, it is particularly useful to include cetyl esters in the hair conditioning compositions. Cetyl Esters is a mixture of the following esters of saturated fatty acids and fatty alcohols:cetyl palmitate, cetyl stearate, myristyl myristate, myristyl stearate, cetyl myristate, and stearyl stearate.

Esters of $C_4$-$C_{22}$ dicarboxylic or tricarboxylic acids and of $C_1$-$C_{22}$ alcohols and esters of monocarboxylic, dicarboxylic or tricarboxylic acids and of $C_4$-$C_{26}$ dihydroxy, trihydroxy, tetrahydroxy or pentahydroxy non-sugar alcohols may also be used. Mention may be made in particular of diethyl sebacate; diisopropyl sebacate; diisopropyl adipate; di-n-propyl adipate; triisopropyl citrate; glyceryl trilactate; glyceryl trioctanoate; neopentyl glycol diheptanoate; and diethylene glycol diisononanoate.

Non-limiting liquid esters (ester oils) or liquid fatty esters that may be mentioned include, for example, sunflower oil, corn oil, soybean oil, marrow oil, grapeseed oil, sesame seed oil, hazelnut oil, apricot oil, macadamia oil, arara oil, castor oil, avocado oil, olive oil, rapeseed oil, coconut oil, wheatgerm oil, sweet almond oil, apricot oil, safflower oil, candlenut oil, coconut oil, camellina oil, tamanu oil, babassu oil and pracaxi oil, jojoba oil, and shea butter oil.

The esters of the present disclosure may also further comprise solid fatty acid esters and/or fatty acid esters including solid esters obtained from $C_9$-$C_{26}$ fatty acids and from $C_9$-$C_{25}$ fatty alcohols. Among these esters, mention may be made of octyldodecyl behenate, isocetyl behenate, cetyl lactate, stearyl octanoate, octyl octanoate, cetyl octanoate, decyl oleate, myristyl stearate, octyl palmitate, octyl pelargonate, octyl stearate, alkyl myristates such as cetyl myristate, myristyl myristate or stearyl myristate, and hexyl stearate.

In an embodiment, the one or more esters of the cosmetic composition of the present disclosure include one or more diesters, in particular, diester oils, chosen from diisostearyl malate, neopentyl glycol dioctanoate, dibutyl sebacate, di-$C_{12-13}$ alkyl malate, dicetearyl dimer dilinoleate, dicetyl adipate, diisocetyl adipate, diisononyl adipate, diisostearyl dimer dilinoleate, diisostearyl fumarate, and mixtures thereof.

Kits

Aspects of the instant disclosure are directed to kits, which include cosmetic compositions as discussed herein. In an embodiment, the cosmetic compositions of the instant disclosure are hair cosmetic or hair treatment compositions. For example, kits may include at least one cosmetic composition according to the instant disclosure, such as a hair cosmetic or a hair treatment composition, and one or more additional compositions, such as a shampoo, a conditioner, etc. The various compositions are separately contained in the kits. In some instances, the kits include one or more cosmetic compositions, such as a hair cosmetic or a hair treatment composition, according the instant disclosure, a shampoo, a conditioner, a mask, and/or other hair treatment products, all of which are separately contained.

The cosmetic compositions of the kit may be packaged in a variety of different containers, such as, for example, a ready-to-use container. Non-limiting examples of useful packaging include tubes, jars, caps, unit dose packages, and bottles, including squeezable tubes, bottles, and sprayable containers. The packaging may be configured so that it can be attached to a wall, such as a wall in a bathroom, including walls of a shower or tub. For example, the packaging can be a container that is configured to attach to a wall, such that when pressure is applied to the container, the composition contained therein is expelled from one or more openings in the container. In some cases, the packaging is a tube, such as a tube with two compartments, or dual tubes, each forming a separate compartment. Each compartment may include a different composition. For example, one tube or compartment may include a cosmetic composition according to the instant disclosure, and the other tube may include a composition to be used with the cosmetic composition, for example, a shampoo, a conditioner, an all-in-one shampoo/conditioner (i.e., a conditioning shampoo; also referred to as a "co-wash") mask or other cosmetic products.

Method(s) for producing cosmetic compositions

Aspects of the disclosure relate to methods for producing cosmetic compositions. The methods for producing cosmetic compositions typically include:
(I) producing a deep eutectic solvent system comprising:
(i) citric acid, and
(ii) a urea compound,
wherein a mole ratio of the citric acid of (i) to the urea compound of (ii) is about 10:0.5 to about 0.5:10; and (II) adding the deep eutectic solvent system of (I) to a base composition comprising:
  (a) about 20 to about 95 wt. %, based on the weight of the base composition, of a polyol;
  (b) about 5 to about 70 wt. %, based on the weight of the base composition, of one or more monoalcohols having from 2 to 6 carbon atoms;
    wherein the weight ratio of the polyol to the monoalcohol(s) (polyol:monoalcohol(s)) is from 20:1 to 1:20;
  (c) about 0.1 to about 10 wt. %, based on the weight of the base composition, of one or more cationic surfactants; and
  (d) about 0.1 to about 20 wt. %, based on the weight of the base composition, of one or more fatty compounds.

The method may further include forming the deep eutectic solvent (DES) system of (I) by mixing the citric acid of (i) and the urea compound of (ii) in certain ratios, e.g., as discussed herein. In some cases, the DES system may be formed at room temperatures, e.g., when the citric acid and urea compounds mix as liquids at room temperature. In other cases, the method includes heating a mixture/combination of the citric acid and the urea compound to a temperature of about 70° C. to about 90° C. Heating the mixture/combination of citric acid and urea compounds is typically beneficial when the citric acid and urea compounds do not mix as liquids at room temperature. The mixture/combination of citric acid and urea compounds may be heated to a temperature, such that the citric acid and urea compounds mix as liquids. For instance, the mixture/combination of citric acid and urea compounds may be heated to a temperature of about 75° C. to about 90° C., about 80° C. to about 90° C., about 85° C. to about 90° C., about 70° C. to about 85° C., about 75° C. to about 85° C., about 80° C. to about 85° C., about 70° C. to about 80° C., about 75° C. to about 80° C., or about 70° C. to about 75° C., or any ranges or subranges thereof.

The method may include producing a base composition of the cosmetic composition by combining one or more of the polyol of (a), monoalcohol having from 2 to 6 carbon atoms of (b), cationic surfactant of (c), and fatty compounds of (d). One of ordinary skill would understand how to combine the foregoing compounds such that the base of the composition is stable and/or uniform. In some cases, the base of the cosmetic composition may be heated, mixed, and/or receive shear forces, e.g., from an emulsifier.

Method(s) for Treating Keratinous Substrates

Aspects of the instant disclosure also relate to methods for using such cosmetic compositions.

A method for treating keratinous substrates such as hair or skin according to aspects of the disclosure typically includes:
  (I) applying onto a keratinous substrate, a cosmetic composition comprising:
    (a) about 20 to about 95 wt. % of a polyol;
    (b) about 5 to about 70 wt. % of one or more monoalcohols having from 2 to 6 carbon atoms;
      wherein the weight ratio of the polyol to the monoalcohol(s) (polyol:monoalcohol(s)) is from 20:1 to 1:20;
    (c) about 0.1 to about 10 wt. % of one or more cationic surfactants;
    (d) about 0.1 to about 20 wt. % of one or more fatty compounds; and
    (e) about 1 to about 15 wt. % of a combination of:
      (i) citric acid, and
      (ii) a urea compound,
        wherein a mole ratio of the citric acid of (i) to the urea compound of (ii) is about 10:0.5 to about 0.5:10, and all weight percentages are based on the total weight of the cosmetic composition; and
  (Ii) optionally, rinsing the keratinous substrate to remove at least a portion of the cosmetic composition;
  wherein the keratinous substrate is wet or rinsed with extraneous water before and/or after and/or during the application of the cosmetic composition onto the substrate, A method for treating hair according to aspects of the disclosure typically includes:
  (I) optionally, applying a shampoo to hair;
  (II) optionally, rinsing the hair to remove at least a portion of the shampoo;
  (III) applying a cosmetic composition comprising:
    (a) about 20 to about 95 wt. % of a polyol;
    (b) about 5 to about 70 wt. % of one or more monoalcohols having from 2 to 6 carbon atoms;
      wherein the weight ratio of the polyol to the monoalcohol(s) (polyol:monoalcohol(s)) is from 20:1 to 1:20;
    (c) about 0.1 to about 10 wt. % of one or more cationic surfactants;
    (d) about 0.1 to about 20 wt. % of one or more fatty compounds; and
    (e) about 1 to about 15 wt. % of a combination of:
      (i) citric acid, and
      (ii) a urea compound,
        wherein a mole ratio of the citric acid of (i) to the urea compound of (ii) is about 10:0.5 to about 0.5:10, and all weight percentages are based on the total weight of the cosmetic composition; and
  (IV) optionally, rinsing the hair to remove at least a portion of the cosmetic composition.

The methods for treating and/or cleaning hair according to the disclosure may vary but typically include applying a cosmetic composition as disclosed herein, allowing the cosmetic composition to remain on the hair for a sufficient amount of time, and rinsing the cosmetic compositions from the hair. In some instances, however, the cosmetic composition may be a leave-in composition. For example, the cosmetic compositions may be allowed to remain on the hair indefinitely, i.e., the cosmetic composition is not removed or rinsed from the hair prior to styling the hair.

The cosmetic composition may be applied to the hair in a sequence with other compositions. For example, the cosmetic composition may be applied to the hair before shampooing the hair, after shampooing the hair, before conditioning the hair, and/or after conditioning the hair, etc. The cosmetic compositions, however, are not required to be used in a sequence.

The methods may include applying an amount of the cosmetic composition onto keratinous substrates such as hair or skin, for example, onto one or both hands, onto the hair, onto the scalp, onto the face, onto the body, etc. The hair or skin may already be wet or damp with extraneous water or extraneous water can be included after the cosmetic composition has already been applied to the hair or skin. The cosmetic composition and the extraneous water may optionally be mixed together on the skin of the body or hair to facilitate formation of an opaque emulsion, lamellar phase structure, and/or mixed structure having an increased viscosity. Alternatively, the cosmetic composition and extraneous water may be combined, and optionally mixed, prior to application to the hair or skin. For example, the cosmetic composition may be combined in a container, bowl, packaging, bottle, etc., and subsequently applied to the hair or skin after formation of the opaque emulsion.

In some instances, the methods include forming the lamellar phase structure, mixed structure, and/or an opaque emulsion on the hands and subsequently applying it to the hair or skin. In other instances, the methods include forming the lamellar phase structure, mixed structure, and/or an opaque emulsion directly on the hair or skin. When the keratinous substrate to be treated is hair, the cosmetic compositions and the emulsions formed by combination with water are useful for conditioning, managing the hair, improving durability of cosmetic effects, and/or improving the hair's resistance to thermal degradation. The cosmetic compositions and the emulsions formed by combination of water can be applied to the wet or damp hair and may be massaged into the hair, for example, with the hands, and/or spread throughout the hair with a comb or brush. This results in a smoothing and softening of the hair, which reduces frizz, dryness, and unwanted volume.

In some cases, the cosmetic compositions are used in conjunction with additional hair-care or skin care or skin cleansing compositions in a routine, for example, during an individual's normal showering/bathing/cleansing routine. The cosmetic composition may be applied to the hair or skin individually or may be combined with one or more additional compositions. For instance, the cosmetic composition may be mixed with a shampoo (or conditioner) prior to application to the hair. In this case, the mixture of the shampoo (or conditioner) and the cosmetic composition are simultaneously applied to the hair during the cleansing or conditioning process and simultaneously rinsed from the hair. Alternatively, the cosmetic composition may be layered on top of (or lathered into) hair to which a shampoo (or conditioner) has already been applied or vice versa. In this case, the cosmetic composition may be applied to the hair and without rinsing it from the hair, a shampoo (or conditioner) is then subsequently applied to the hair. Alternatively, the shampoo (or conditioner) may be first applied to the hair and without rinsing the shampoo (or conditioner) from the hair, the cosmetic composition is also applied to the hair.

When used in conjunction with a shampoo and/or a conditioner, the cosmetic composition may be mixed or used with the shampoo and/or conditioner in a ratio of about 1:10 to about 10:1, about 1:5 to about 5:1, about 1:3 to about 3:1, about 1:2 to about 2:1, about 1:1 to about 4:1, about 1:1 to about 3:1, or about 1:1 to about 2:1 (cosmetic composition of the instant disclosure: shampoo/conditioner, etc.).

The cosmetic compositions of the instant disclosure may be allowed to remain on the hair for a minimum amount of time before being rinsed from the hair, but it is not necessary to allow the cosmetic composition to remain on the hair for an extended period of time. Conveniently, the cosmetic compositions can be applied and allowed to remain on the hair for a period of time that is typical for regular shampooing and/or conditioning. For example, the cosmetic composition (whether combined with another hair-treatment composition such as a shampoo or conditioner) may be applied to the hair and allowed to remain on the hair for a few seconds (1, 2, 3, or 5 seconds) up to about 1, about 2, about 5, about 10, about 15, about 20, about 25, or about 30 minutes.

When the cosmetic composition is not being mixed with another composition prior to application to the hair, the cosmetic composition may be applied to the hair immediately after or before the hair is treated with another composition (e.g., a shampoo and/or a conditioner). For example, the cosmetic compositions may be applied to the hair within about a few seconds or 1, 2, 5, 10, or 20 minutes before or after a shampoo and/or a conditioner is applied to the hair.

The term "INCI" is an abbreviation of International Nomenclature of Cosmetic Ingredients, which is a system of names provided by the International Nomenclature Committee of the Personal Care Products Council to describe personal care ingredients.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

All components and elements positively set forth in this disclosure can be negatively excluded from the claims. In other words, the hair cleansing compositions of the instant disclosure can be free or essentially free of all components and elements positively recited throughout the instant disclosure. In some instances, the hair cleansing compositions of the present disclosure may be substantially free of non-incidental amounts of the ingredient(s) or compound(s) described herein. A non-incidental amount of an ingredient or compound is the amount of that ingredient or compound that is added into the hair cleansing composition by itself. For example, a hair cleansing composition may be substantially free of a non-incidental amount of an ingredient or compound, although such ingredient(s) or compound(s) may be present as part of a raw material that is included as a blend of two or more compounds.

Some of the various categories of components identified may overlap. In such cases where overlap may exist and the hair cleansing composition includes both components (or the composition includes more than two components that overlap), an overlapping compound does not represent more than one component. For example, certain compounds may be characterized as both an emulsifier and a surfactant. If a particular hair composition includes both an emulsifier and a surfactant, the compounds that may be characterized as both an emulsifier and a surfactant will serve only as either the emulsifier or the surfactant—not both.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

As used herein, the terms "comprising," "having," and "including" are used in their open, non-limiting sense. The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

The expression "one or more" means "at least one" and thus includes individual components as well as mixtures/combinations. Other than in the operating examples, or where otherwise indicated, all numbers expressing quantities of ingredients and/or reaction conditions may be modified in all instances by the term "about," meaning within +/−5% of the indicated number.

As used herein, all weight percent (or wt. %) expressed or mentioned are based on 100% activity unless described or indicated otherwise.

The term "treat" (and its grammatical variations) as used herein refers to the application of the compositions of the present disclosure onto the surface of keratinous substrates such as hair on a user's head and/or body.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material. All of the components set forth herein may be optionally included or excluded from the compositions/method/kits. When excluded, the compositions/methods/kits may be free or essentially free of the component. For example, a particular composition may be free or essentially free of silicones.

EMBODIMENTS OF THE DISCLOSURE

In certain embodiments, the cosmetic composition includes:
- about 20 to about 95 wt. %, preferably about 20 to about 85 wt. %, more preferably about 30 to about 70 wt. %, of a polyol, such as those chosen from ethylene glycol, propylene glycol, butylene glycol, hexylene glycol, pentylene glycol, 1,3-propanediol, diethylene glycol, dipropylene glycol, 1,4-butanediol, 1,5-pentanediol, hexane-1,6-diol, glycerin, diglycerin, caprylyl glycol, polyethylene glycols, and a mixture thereof;
- about 5 to about 70 wt. %, preferably about 5 to about 50 wt. %, more preferably about 5 to about 40 wt. %, of one or more monoalcohols having from 2 to 6 carbon atoms including, e.g., ethanol, propanol, butanol, pentanol, hexanol, isopropyl alcohol, cyclohexanol, isobutyl alcohol, 2-methyl-2-butanol (2-methylbutan-2-ol), and a mixture thereof;
- wherein the weight ratio of the polyol to the monoalcohol(s) (polyol:monoalcohol(s)) is from 20:1 to 1:20, preferably about 15:1 to about 1:20, more preferably about 15:1 to about 1:15;
- about 0.1 to about 10 wt. %, preferably about 0.1 to about 8 wt. %, more preferably about 0.2 to about 8 wt. %, of one or more cationic surfactants, such as cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyldiethylamine, arachidamidoethyidiethylamine, arachidamidoethyidimethylamine, and mixtures thereof;
- about 0.1 to about 20 wt. %, preferably about 0.1 to about 16 wt. %, more preferably about 0.5 to about 16 wt. %, of one or more fatty compounds including, e.g., a fatty alcohol, a fatty ester, a fatty ether, a fatty acid, a wax, an oil, a derivative thereof, or a mixture thereof; and
- about 1 to about 15 wt. %, preferably about 1 to about 10 wt. %, more preferably about 3 to about 7 wt. %, of a combination of:
  (i) citric acid, preferably in an amount of about 0.5 to about 12 wt. % or more preferably in an amount of about 1 to about 10 wt. %, and
  (ii) a urea compound, preferably in an amount of about 0.5 to about 12 wt. % or more preferably in an amount of about 1 to about 10 wt. %, wherein the urea compounds may be chosen from imidazolidinyl urea, diazolidinyl urea, m-dimethylaminophenyl urea, dimethyl urea, a hydroxyethyl urea, urea, urea derivatives, imidazolidinyl urea, diazolidinyl urea, m-dimethylaminophenyl urea, dimethyl urea, a hydroxyethyl urea, N-(2-hydroxyethyl)urea; N-(2-hydroxypropyl)urea; N-(3-hydroxypropyl)urea; N-(2,3-dihydroxypropyl)urea; N-(2,3,4,5,6-pentahydroxyhexyl)urea; N-methyl-N-(1,3,4,5,6-pentahydroxy-2-hexyl)urea; N-methyl-N'-(1-hydroxy-2-methyl-2-propyl)urea; N-(1-hydroxy-2-methyl-2-propyl)urea; N-(1,3-dihydroxy-2-propyl)urea; N-(tris-hydroxymethylmethyl)urea; N-ethyl-N'-(2-hydroxyethyl)urea; N,N-bis(2-hydroxyethyl)urea; N,N'-bis(2-hydroxyethyl)urea; N,N-bis(2-hydroxypropyl) urea; N,N'-bis(2-hydroxypropyl)urea; N,N-bis(2-hydroxyethyl)-N'-propylurea; N,N-bis(2-hydroxypropyl)-N'-(2-hydroxyethyl)urea; N-tert-butyl-N'-(2-hydroxyethyl)-N'-(2-hydroxypropyl)urea; N-(1,3-dihydroxy-2-propyl)-N'-(2-hydroxyethyl)urea; N,N-bis(2-hydroxyethyl).-N',N'-dimethylurea; N,N,N',N'-tetrakis(2-hydroxyethyl)urea; N',N'-bis(2-hydroxyethyl)-N', N'-bis(2-hydroxypropyl)-urea, and a mixture thereof, wherein a mole ratio of the citric acid of (i) to the urea compound of (ii) is about 10:0.5 to about 0.5:10, or about 8:1 to about 1:8, or preferably about 5:1 to about 1:5, or more preferably about 4:1 to about 1:4, or even more preferably about 3:1 to about 1:3, and all weight percentages are based on the total weight of the cosmetic composition.

In further embodiments, the cosmetic composition for treating keratinous substrates includes:
- about 20 to about 95 wt. %, preferably about 20 to about 80 wt. %, more preferably about 35 to about 70 wt. %, of a polyol chosen from ethylene glycol, propylene glycol, butylene glycol, hexylene glycol, pentylene glycol, diethylene glycol, dipropylene glycol, 1,3 propanediol, glycerin, and a mixture thereof;
- about 5 to about 70 wt. %, preferably about 5 to about 40 wt. %, more preferably about 5 to about 30 wt. %, of one or more monoalcohols having from 2 to 6 carbon atoms including, e.g., ethanol, propanol, butanol, pentanol, hexanol, isopropyl alcohol, cyclohexanol, isobutyl alcohol, 2-methyl-2-butanol (2-methylbutan-2-ol), and a mixture thereof;
- wherein the weight ratio of the polyol to the monoalcohol(s) (polyol:monoalcohol(s)) is from 20:1 to 1:20, preferably about 15:1 to about 1:20, more preferably about 15:1 to about 1:15;
- about 0.1 to about 10 wt. %, preferably about 0.1 to about 6 wt. %, more preferably about 0.2 to about 6 wt. %, of one or more cationic surfactants, such as cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and mixtures thereof;

about 0.1 to about 20 wt. %, preferably about 0.1 to about 14 wt. %, more preferably about 0.5 to about 14 wt. %, of one or more fatty compounds including, e.g., a fatty alcohol, a fatty ester, a fatty ether, a fatty acid, a wax, an oil, a derivative thereof, or a mixture thereof; and about 1 to about 15 wt. %, preferably about 1 to about 10 wt. %, more preferably about 3 to about 7 wt. %, of a combination of:

(i) citric acid, preferably in an amount of about 0.5 to about 12 wt. % or more preferably in an amount of about 1 to about 10 wt. %, and (ii) a urea compound, preferably in an amount of about 0.5 to about 12 wt. % or more preferably in an amount of about 1 to about 10 wt. %, wherein the urea compounds may be chosen from imidazolidinyl urea, diazolidinyl urea, m-dimethylaminophenyl urea, dimethyl urea, a hydroxyethyl urea, urea, urea derivatives, imidazolidinyl urea, diazolidinyl urea, m-dimethylaminophenyl urea, dimethyl urea, a hydroxyethyl urea, N-(2-hydroxyethyl)urea; N-(2-hydroxypropyl)urea; N-(3-hydroxypropyl)urea; N-(2,3-dihydroxypropyl)urea; N-(2,3,4,5,6-pentahydroxyhexyl)urea; N-methyl-N-(1,3,4,5,6-pentahydroxy-2-hexyl)urea; N-methyl-N'-(1-hydroxy-2-methyl-2-propyl)urea; N-(1-hydroxy-2-methyl-2-propyl)urea; N-(1,3-dihydroxy-2-propyl)urea; N-(tris-hydroxymethylmethyl)urea; N-ethyl-N'-(2-hydroxyethyl)urea; N,N-bis(2-hydroxyethyl)urea; N,N'-bis(2-hydroxyethyl)urea; N,N-bis(2-hydroxypropyl)urea; N,N'-bis(2-hydroxypropyl)urea; N,N-bis(2-hydroxyethyl)-N'-propylurea; N,N-bis(2-hydroxypropyl)-N'-(2-hydroxyethyl)urea; N-tert-butyl-N'-(2-hydroxyethyl)-N'-(2-hydroxypropyl)urea; N-(1,3-dihydroxy-2-propyl)-N'-(2-hydroxyethyl)urea; N,N-bis(2-hydroxyethyl).-N',N'-dimethylurea; N,N,N',N'-tetrakis(2-hydroxyethyl)urea; N',N'-bis(2-hydroxyethyl)-N',N'-bis(2-hydroxypropyl)-urea, and a mixture thereof, wherein a mole ratio of the citric acid of (i) to the urea compound of (ii) is about 10:0.5 to about 0.5:10, preferably about 8:1 to about 1:8, or preferably about 5:1 to about 1:5, or more preferably about 4:1 to about 1:4, or even more preferably about 3:1 to about 1:3, and all weight percentages are based on the total weight of the cosmetic composition.

In yet further embodiments, a method for producing cosmetic compositions includes:

(I) producing a deep eutectic solvent system comprising:

(i) citric acid, preferably in an amount of about 0.5 to about 12 wt. % or more preferably in an amount of about 1 to about 10 wt. %, and (ii) a urea compound, preferably in an amount of about 0.5 to about 12 wt. % or more preferably in an amount of about 1 to about 10 wt. %, wherein the urea compounds may be chosen from imidazolidinyl urea, diazolidinyl urea, m-dimethylaminophenyl urea, dimethyl urea, a hydroxyethyl urea, urea, urea derivatives, imidazolidinyl urea, diazolidinyl urea, m-dimethylaminophenyl urea, dimethyl urea, a hydroxyethyl urea, N-(2-hydroxyethyl)urea; N-(2-hydroxypropyl)urea; N-(3-hydroxypropyl)urea; N-(2,3-dihydroxypropyl)urea; N-(2,3,4,5,6-pentahydroxyhexyl)urea; N-methyl-N-(1,3,4,5,6-pentahydroxy-2-hexyl)urea; N-methyl-N'-(1-hydroxy-2-methyl-2-propyl)urea; N-(1-hydroxy-2-methyl-2-propyl)urea; N-(1,3-dihydroxy-2-propyl)urea; N-(tris-hydroxymethylmethyl)urea; N-ethyl-N'-(2-hydroxyethyl)urea; N,N-bis(2-hydroxyethyl)urea; N,N'-bis(2-hydroxyethyl)urea; N,N-bis(2-hydroxypropyl)urea; N,N'-bis(2-hydroxypropyl)urea; N,N-bis(2-hydroxyethyl)-N'-propylurea; N,N-bis(2-hydroxypropyl)-N'-(2-hydroxyethyl)urea; N-tert-butyl-N'-(2-hydroxyethyl)-N'-(2-hydroxypropyl)urea; N-(1,3-dihydroxy-2-propyl)-N'-(2-hydroxyethyl)urea; N,N-bis(2-hydroxyethyl).-N',N'-dimethylurea; N,N,N',N'-tetrakis(2-hydroxyethyl)urea; N',N'-bis(2-hydroxyethyl)-N',N'-bis(2-hydroxypropyl)-urea, and a mixture thereof, wherein a weight ratio of the citric acid of (i) to the urea compound of (ii) is about 3:1 to about 1:3; and (II) adding the deep eutectic solvent system of (I) to a base composition comprising:

about 20 to about 95 wt. %, preferably about 20 to about 85 wt. %, more preferably about 30 to about 70 wt. %, of a polyol, such as those chosen from ethylene glycol, propylene glycol, butylene glycol, hexylene glycol, pentylene glycol, 1,3-propanediol, diethylene glycol, dipropylene glycol, 1,4-butanediol, 1,5-pentanediol, hexane-1,6-diol, glycerin, diglycerin, caprylyl glycol, polyethylene glycols, and a mixture thereof;

about 5 to about 70 wt. %, preferably about 5 to about 50 wt. %, more preferably about 5 to about 40 wt. %, of one or more monoalcohols having from 2 to 6 carbon atoms including, e.g., ethanol, propanol, butanol, pentanol, hexanol, isopropyl alcohol, cyclohexanol, isobutyl alcohol, 2-methyl-2-butanol (2-methylbutan-2-ol), and a mixture thereof;

wherein the weight ratio of the polyol to the monoalcohol(s) (polyol:monoalcohol(s)) is from 20:1 to 1:20, preferably about 15:1 to about 1:20, more preferably about 15:1 to about 1:15;

about 0.1 to about 10 wt. %, preferably about 0.1 to about 8 wt. %, more preferably about 0.2 to about 8 wt. %, of one or more cationic surfactants, such as cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and mixtures thereof; and about 0.1 to about 20 wt. %, preferably about 0.1 to about 16 wt. %, more preferably about 0.5 to about 16 wt. %, of one or more fatty compounds including, e.g., a fatty alcohol, a fatty ester, a fatty ether, a fatty acid, a wax, an oil, a derivative thereof, or a mixture thereof.

EXAMPLES

Implementation of the present disclosure is provided by way of the following examples. The following examples serve to elucidate aspects of the technology without being limiting in nature.

Example 1

Cosmetic compositions were prepared from combinations of the exemplary base composition and the exemplary deep eutectic solvent (DES) systems, shown in Tables 1 and 2. The DES systems was prepared by heating citric acid and urea in the water bath. Specifically, an exemplary cosmetic composition (Exemplary Composition A) was prepared using the methods discussed herein to combine 95 wt. % of the Base Composition and 5 wt. % of the deep eutectic solvent system ("DES") system. A second exemplary cosmetic composition (Exemplary Composition B) was prepared using the methods discussed herein to combine 90 wt. % of the Base Composition and 10 wt. % of the DES system. A third exemplary cosmetic composition (Exemplary Composition C) was prepared using the methods discussed herein to combine 98.5 wt. % of the Base Composition and 1.5 wt. % of the DES system.

The formulation for Exemplary Compositions A-C are shown in Table 3.

TABLE 1

| | | BASE COMPOSITION | |
|---|---|---|---|
| | | INCI US Name | Based on wt.% |
| (a) | Polyol | PROPYLENE GLYCOL | 74.4 |
| (b) | Mono-alcohol | ALCOHOL DENAT. | 20 |
| | Weight ratio of the polyol of (a) to the mono-alcohol of (b) | | 3.72:1 |
| (c) | Cationic Surfactant | STEARAMIDOPROPYL DIMETHYLAMINE | 1.2 |
| (d) | Fatty Compound(s) Fatty Alcohol | CETYL ALCOHOL | 1.5 |
| | Fatty Ester | ISOPROPYL MYRISTATE AND/OR DICAPRYLYL CARBONATE | 1.4 |
| | Fatty Ethers | DICAPRYLYL ETHER | 0.5 |
| | Preservative | TOCOPHEROL | <0.1 |
| | Fragrance | FRAGRANCE | 1 |

TABLE 2

| | | Deep Eutectic Solvent System | | | | |
|---|---|---|---|---|---|---|
| | | INCI US Name | | Based on wt.% | | |
| (i) | Citric Acid | CITRIC ACID | 60 | 55 | 38 | 48 | 65 |
| (ii) | Urea | N,N DIMETHYL UREA | 40 | | | | |
| | | HYDROXYETHYL UREA (45% ACTIVE IN WATER) | | 45 | 62 | 52 | 35 |
| | Mole ratio of the citric acid of (i) to the urea of (ii) (based on active wt.) | | 2:3 | 2:1.35 | 1:1.35 | 1:0.9 | 1:0.45 |

TABLE 3

| | | | Cosmetic Compositions | | | | | | |
|---|---|---|---|---|---|---|---|---|---|
| | | | INCI US Name | Ex. A | Ex. B | Ex. C | Ex. D | Ex. E | Ex. F |
| (a) | Polyol | | PROPYLENE GLYCOL | 70.7 | 67 | 73.3 | 70.7 | 70.7 | 70.7 |
| (b) | Mono-alcohol | | ALCOHOL DENAT. | 19 | 18 | 19.7 | 19 | 19 | 19 |
| | Weight ratio of the polyol of (a) to the mono-alcohol of (b) | | | 3.72:1 | 3.72:1 | 3.72:1 | 3.72:1 | 3.72:1 | 3.72:1 |
| (c) | Cationic Surfactant | | STEARAMIDOPROPYL DIMETHYLAMINE | 1.14 | 1.08 | 1.18 | 1.14 | 1.14 | 1.14 |
| (d) | Fatty Compound(s) | Fatty Alcohol | CETYL ALCOHOL | 1.425 | 1.35 | 1.48 | 1.425 | 1.425 | 1.425 |
| | | Fatty Ester | ISOPROPYL MYRISTATE and DICAPRYLYL CARBONATE | 1.33 | 1.26 | 1.38 | 1.33 | 1.33 | 1.33 |
| | | Fatty Ethers | DICAPRYLYL ETHER | 0.475 | 0.45 | 0.49 | 0.475 | 0.475 | 0.475 |
| | Preservative | | TOCOPHEROL | <0.1 | <0.1 | <0.1 | <0.1 | <0.1 | <0.1 |
| | Fragrance | | FRAGRANCE | 0.95 | 0.9 | 0.99 | 0.95 | 0.95 | 0.95 |
| (e) | (i) | Citric Acid | CITRIC ACID | 3 | 6 | 0.9 | 2.75 | 1.9 | 2.4 |
| | (ii) | Urea | N,N DIMETHYL UREA | 2 | 4 | 0.6 | | | |
| | | | Hydroxyethyl Urea (45% active in water) | | | | 2.24 | 3.1 | 2.6 |
| | mole ratio of the citric acid of (i) to the urea of (ii) | | | 2:3 | 2:3 | 2:3 | 2:1.35 | 1:1.35 | 1:0.9 |

| | | | INCI US Name | Ex. G | Comp. 1 | Comp. 2 | Comp. 3 | Comp. 4 | Comp. 5 |
|---|---|---|---|---|---|---|---|---|---|
| (a) | Polyol | | PROPYLENE GLYCOL | 70.7 | 74.4 | 72.9 | 72.2 | 73.7 | 74.0 |
| (b) | Mono-alcohol | | ALCOHOL DENAT. | 19 | 20 | 19.6 | 19.4 | 19.8 | 19.9 |
| | Weight ratio of the polyol of (a) to the mono-alcohol of (b) | | | 3.72:1 | 3.72:1 | 3.72:1 | 3.72:1 | 3.72:1 | 3.72:1 |
| (c) | Cationic Surfactant | | STEARAMIDOPROPYL DIMETHYLAMINE | 1.14 | 1.2 | 1.18 | 1.16 | 1.19 | 1.19 |

TABLE 3-continued

| Cosmetic Compositions | | | | | | | | |
|---|---|---|---|---|---|---|---|---|
| (d) | Fatty Compound(s) | Fatty Alcohol | CETYL ALCOHOL | 1.425 | 1.5 | 1.47 | 1.46 | 1.49 | 1.49 |
| | | Fatty Ester | ISOPROPYL MYRISTATE and DICAPRYLYL CARBONATE | 1.33 | 1.4 | 1.37 | 1.36 | 1.39 | 1.39 |
| | | Fatty Ethers | DICAPRYLYL ETHER | 0.475 | 0.5 | 0.49 | 0.49 | ~0.50 | ~0.50 |
| | Preservative | | TOCOPHEROL | <0.1 | <0.1 | <0.1 | <0.1 | <0.1 | <0.1 |
| | Fragrance | | FRAGRANCE | 0.95 | 1 | 0.98 | 0.97 | 0.99 | 0.99 |
| (e) | (i) | Citric Acid | CITRIC ACID | 3.25 | | | 3 | 0.9 | |
| | (ii) | Urea | N,N DIMETHYL UREA | | | 2 | | | 0.6 |
| | | | Hydroxyethyl Urea (45% active in water) | 1.8 | | | | | |
| mole ratio of the citric acid of (i) to the urea of (ii) | | | | 1:0.45 | | | | | |

Example 2

The thermal denaturation temperature and durability effects imparted by Exemplary Compositions A and B to hair were evaluated in comparison to the effects imparted by Comparative Composition 1 and a Control. Comparative Composition 1 has the same formulation as the base composition provided in Table 1, which was used to prepare Exemplary Compositions A and B.

Exemplary Compositions A and B and Comparative Composition 1 were applied to bleached hair swatches. The bleached hair swatches were washed with a conventional sulfate-based shampoo and rinsed before the respective cosmetic compositions were applied in an amount of about 0.1 gram of the respective cosmetic composition per gram of hair swatch. The hair swatches were combed to uniformly spread the respective cosmetic compositions on the hair swatches. After about 1 minute, the hair swatches were rinsed with water. A control was prepared by applying the conventional sulfate-based shampoo without subsequently applying a cosmetic composition to the hair swatch.

The hair swatches were assessed to evaluate the effect of Exemplary Compositions A and B and Comparative Composition 1 on the thermal denaturation temperature and durability of the hair swatches in view of the Control. The hair swatches underwent cyclic fatigue to determine the durability of the hair swatch. The Cyclic Tester simulates every day hair grooming by subjecting fibers to repeated cyclic tensile deformations until failure. Additionally, the hair swatches were evaluated for the thermal denaturation temperature, which is associated with cross-link density of the amorphous matrix, using Differential Scanning calorimetry. Differential scanning calorimetry measures the thermal stability of hair's major morphological components.

Figure 2:
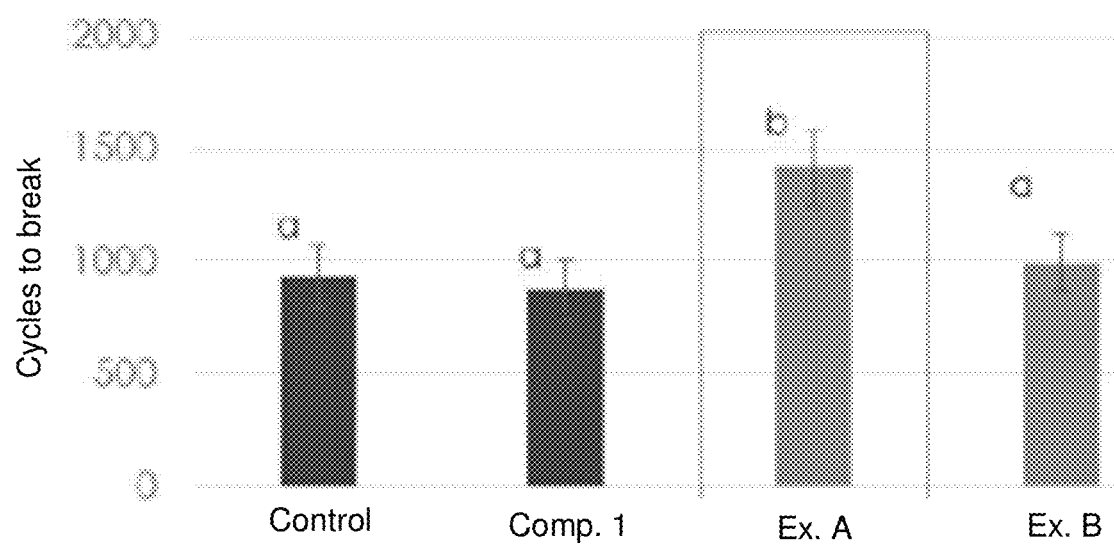
FIG. 2 is a bar graph showing the durability of hair swatches after treatment with comparative compositions and exemplary cosmetic compositions according to aspects of the disclosure.

As seen in FIGS. 1 and 2, the hair swatches that received Exemplary Compositions A and B had a denaturation temperature of about 136° C. and about 137° C., respectively. Comparative Composition 1 and the Control both had a denaturation temperature of about 132° C. The durability of the hair treated with Exemplary Composition A was surprisingly higher than the durability of the hair treated with Comparative Composition 1, and the Control. For example, the durability of hair treated with Exemplary Composition A was about 50% greater than the durability of hair treated with Comparative Composition 1 and the Control. The hair treated with Exemplary Composition B also exhibited a higher durability than the hair treated with Comparative Composition 1 and the Control.

Example 3

The thermal denaturation temperature and durability effects imparted by Exemplary Composition A to hair was evaluated in comparison to the effects imparted by Comparative Compositions 1-3 and a Control. Comparative Composition 2 was prepared by combining 98 wt. % of the Base Composition and 2 wt. % of N,N-dimethyl urea. Comparative Composition 3 was prepared by combining 97 wt. % of the Base Composition and 3 wt. % of citric acid.

Exemplary Composition A and Comparative Compositions 1-3 were applied to bleached hair swatches. The bleached hair swatches were washed with a conventional sulfate-based shampoo and rinsed before the application of Exemplary Composition A and Comparative Compositions 1-3 in an amount of about 0.1 gram of the respective cosmetic composition per gram of hair swatch. The hair swatches were combed to uniformly spread the respective cosmetic formulations on the hair swatches. After about 1 minute, the hair swatches were rinsed with water. A control was prepared according to the above procedure, except that a cosmetic composition was not applied to the respective hair swatch after the conventional sulfate-based shampoo.

The hair swatches were then assessed to evaluate effect of Exemplary Composition A and Comparative Compositions 1-3 on the thermal denaturation temperature, which corresponds to cross-link density, and durability of the hair swatches in view of the control. The thermal denaturation temperature and durability of the hair was determined as discussed in Example 3.

Figure 3:
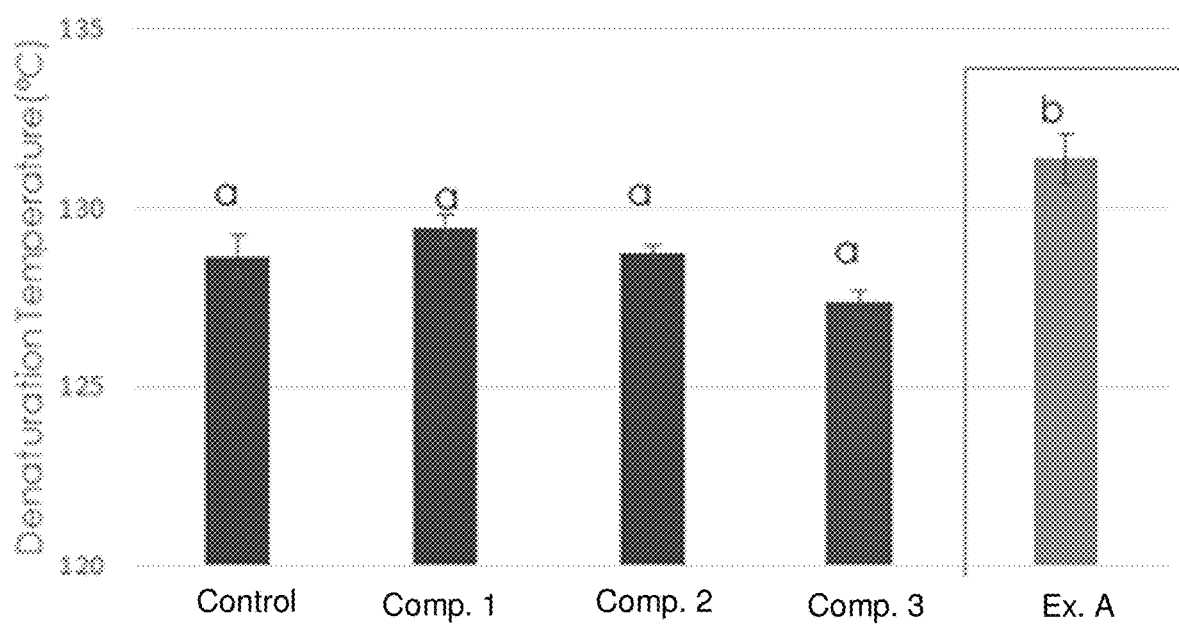
FIG. 3 is a bar graph showing the denaturation temperature of hair swatches after treatment with comparative compositions and exemplary cosmetic composition in accordance with aspects of the disclosure.
Figure 4:
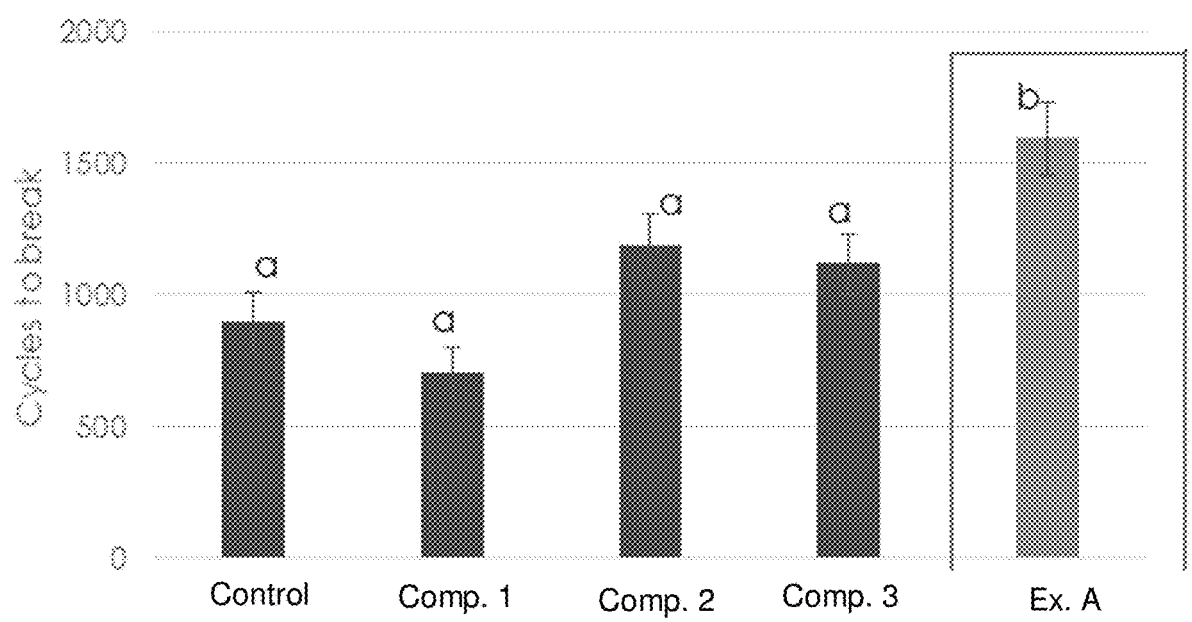
FIG. 4 is a bar graph showing the durability of hair swatches after treatment with comparative compositions and exemplary cosmetic composition according to aspects of the disclosure.

The hair that was treated with Exemplary Composition A exhibited an improved thermal denaturation temperature and significantly improved durability as compared to the hair treated with Comparative Compositions 1-3 and the Control, as seen in FIGS. 3 and 4.

Example 4

The thermal denaturation temperature and durability effects imparted by Exemplary Composition A was evaluated in comparison to the effects imparted to hair by Comparative Compositions 1-3 and a Control. In particular, Exemplary Composition A and Comparative Compositions 1-3 were applied to bleached hair swatches. The bleached hair swatches were washed with a conventional sulfate-based shampoo and rinsed before the application of Exemplary Composition A and Comparative Compositions 1-3 in an amount of about 0.1 gram of the respective cosmetic composition per gram of hair swatch. The hair swatches were combed to uniformly spread the respective cosmetic formulations on the hair swatches. After about 1 minute, the hair swatches were rinsed with water. This procedure of shampooing the hair swatches, rinsing the hair swatches, applying the respective cosmetic compositions, was completed for a total of 6 cycles. A control was prepared according to the above procedure, except that a cosmetic composition was not applied to the respective hair swatch after the conventional sulfate-based shampoo.

The hair swatches were then assessed to evaluate effect of Exemplary Composition A and Comparative Compositions 1-3 on the thermal denaturation temperature, which corresponds to cross-link density, and durability of the hair swatches in view of the Control. The thermal denaturation temperature and durability of the hair was determined as discussed in Example 3.

Figure 5:
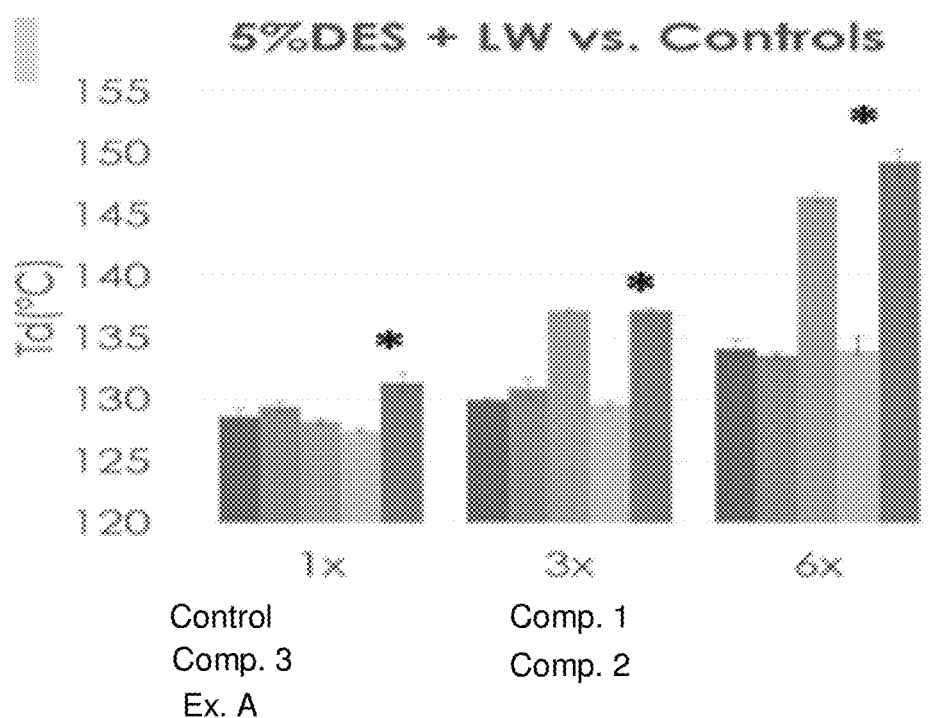
FIG. 5 is a bar graph showing the denaturation temperature of hair swatches after 1, 3, and 6 applications of comparative compositions or an exemplary cosmetic composition in accordance with aspects of the disclosure.
Figure 6:
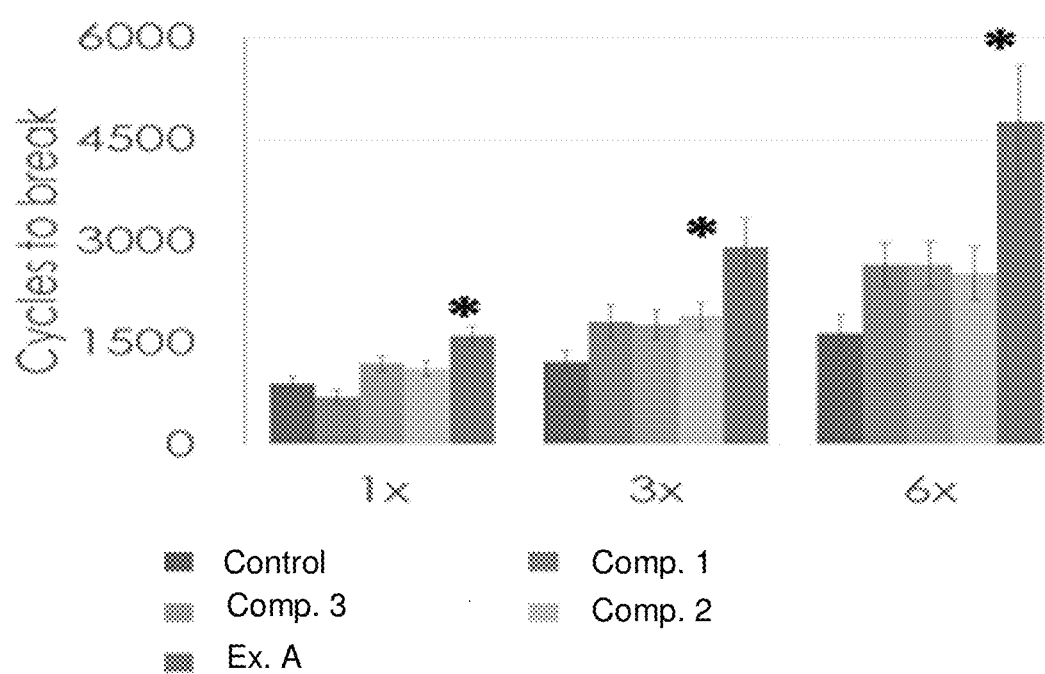
FIG. 6 is a bar graph showing the durability of hair swatches after 1, 3, and 6 applications of comparative compositions and exemplary cosmetic composition according to aspects of the disclosure.

The hair that was treated with Exemplary Composition A exhibited an improved thermal denaturation temperature and significantly improved durability as compared to the hair treated with Comparative Compositions 1-3 and the Control, as seen in FIGS. 5 and 6.

Example 5

Hair swatches treated with Exemplary Compositions A and H were evaluated and compared to hair swatches treated with Comparative composition 1 or only with a conventional sulfate-based shampoo (Control). Exemplary Composition H was prepared by adding a mixture containing 6 wt. % of citric acid and 4 wt. % of dimethyl urea with the remainder of the mixture being water to the base composition of table 1, such the mixture was in amount of 5 wt. % and the base composition was in an amount of 95 wt. % of the total weight of Exemplary Composition H.

Natural brown wavy Caucasian hair swatches, were washed with a conventional sulfate-based shampoo and rinsed before the application of Exemplary Compositions A and H and Comparative Composition 1. An amount of 0.4 gram of each of the compositions per gram of hair swatch was massaged onto their respective hair swatches for 1 minute, left on the hair swatches for another minute, rinsed for 30 seconds, and then blow dried for 2 minutes. These hair swatches were then evaluated to assess the effects of the compositions using a rinse-off procedure. The control was prepared according to the above procedure, except that a cosmetic composition was not applied to the hair swatch after the conventional sulfate-based shampoo.

Additional hair swatches were prepared by applying the test compositions to hair swatches in an amount of 0.15 grams of composition per gram of respective hair swatches. Specifically, Exemplary Compositions A and H and Comparative Composition 1 were massaged onto their respective hair swatches for one minute, left on the hair swatches for a minute, and then below dried for two minutes. These hair swatches were evaluated to assess the effects of the test compositions using a leave-on procedure.

Anti-frizz properties or the degree of frizz on each of the hair swatches was evaluated using imaging analysis. Anti-frizz properties of the hair swatches were measured after the hair swatches were blow dried and after 1 hour of the hair swatches residing in a humidity chamber at 80% relative humidity and room temperature.

Figure 7A:
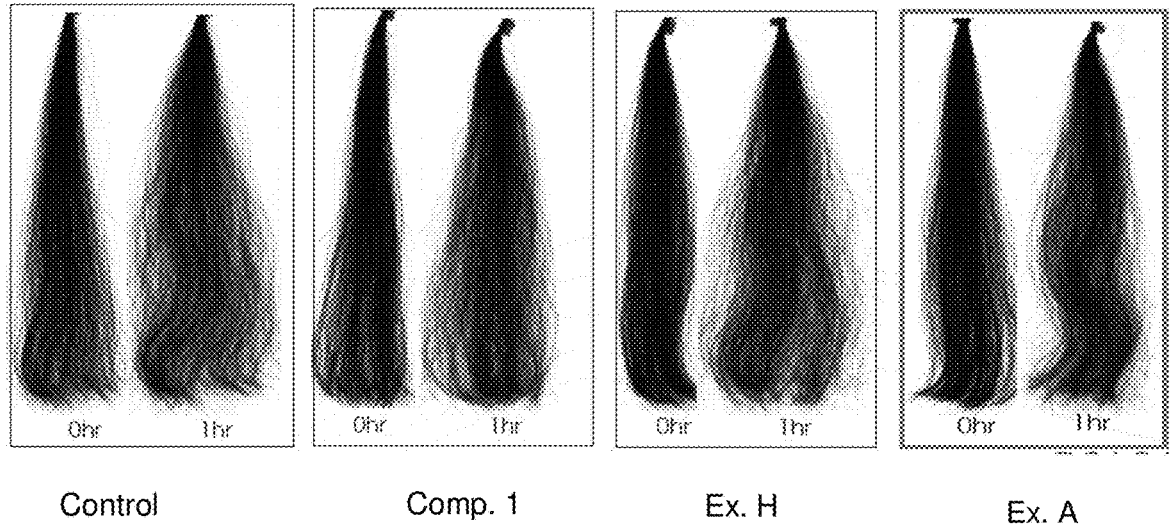
FIGS. 7A and 7B are pictures of hair swatches treated with compositions according to the instant disclosure and comparative composition subjected to humidity in accordance with aspects of the disclosure.
Figure 7B:
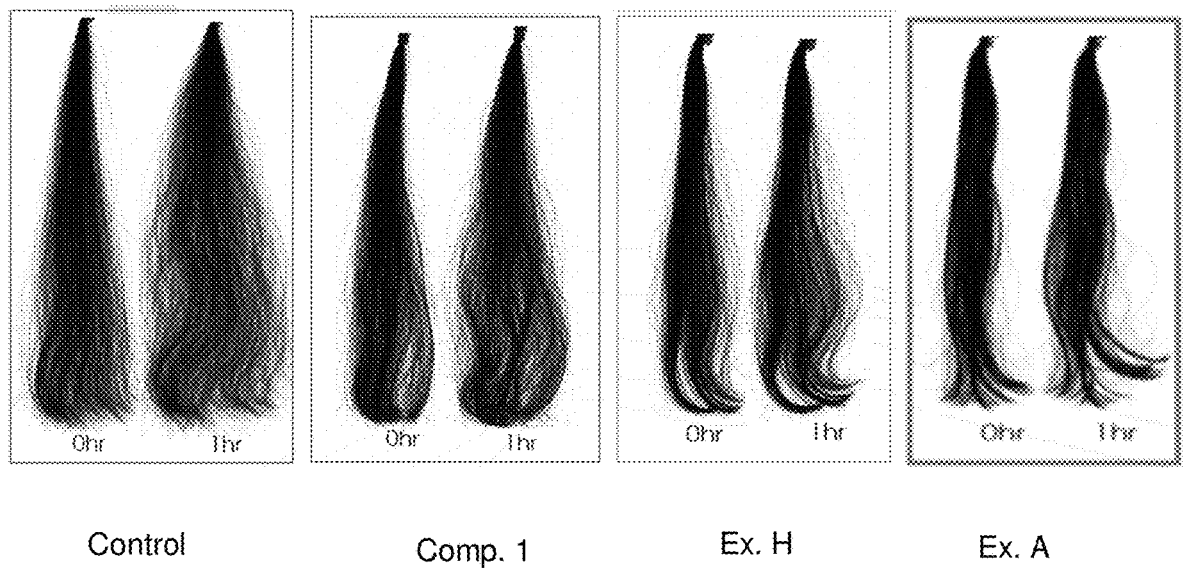

Surprisingly, for both the rinse-off and leave-in procedures, the swatches treated with Exemplary Composition A exhibited significantly better anti-frizz properties after the treatment and at one hour after treatment compared to the swatches treated with Comparative Composition 1 or the Control, as shown in FIGS. 7A and 7B. In addition, for both the rinse-off and leave-in procedures, Exemplary Composition H exhibited significantly better anti-frizz properties after treatment compared to the swatches treated with Composition 1 or the Control. For the leave-in procedure, Exemplary Composition H exhibited better anti-frizz properties at one hour after treatment compared to the swatches treated with Comparative Composition 1 or the Control.

Example 6

The thermal denaturation temperature and durability effects imparted by Exemplary Composition C to hair was evaluated in comparison to the effects imparted by Comparative Compositions 1, 4, and 5 and a Control. Comparative Composition 4 was prepared by combining 99.1 wt. % of the Base Composition and 0.9 wt. % of citric acid. Comparative Composition 5 was prepared by combining 99.4 wt. % of the Base Composition and 0.6 wt. % of N,N-dimethyl urea.

Specifically, Exemplary Composition C and Comparative Compositions 1, 4, and 5 were applied to bleached hair swatches. The bleached hair swatches were washed with a conventional sulfate-based shampoo and rinsed before the application of Exemplary Composition C and Comparative Compositions 1, 4, and 5 in an amount of about 0.1 gram of the respective cosmetic composition per gram of hair swatch. The hair swatches were combed to uniformly spread the respective cosmetic formulations on the hair swatches. After about 1 minute, the hair swatches were rinsed with water. This procedure of shampooing the hair swatches, rinsing the hair swatches, applying the respective cosmetic compositions, was completed for a total of 6 cycles. A control was prepared according to the above procedure, except that a cosmetic composition was not applied to the respective hair swatch after the conventional sulfate-based shampoo.

The hair was then assessed to evaluate effect of Exemplary Composition C and Comparative Compositions 1, 4, and 5 on the thermal denaturation temperature, which corresponds to cross-link density, and durability of the hair in view of the Control. The thermal denaturation temperature and durability of the hair was determined as discussed in Example 3.

Figure 8:
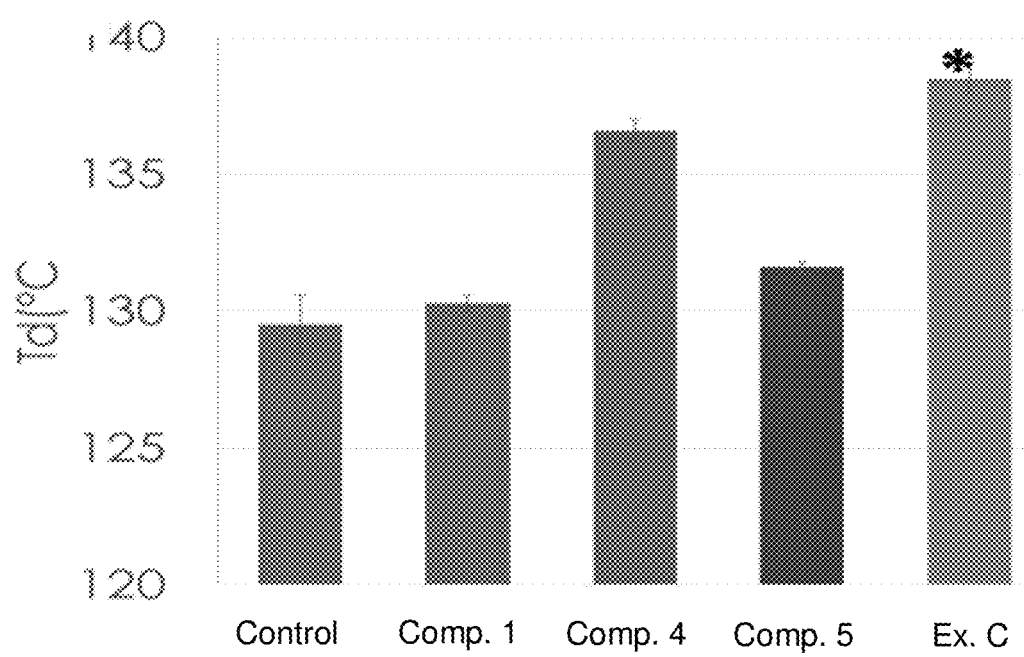
FIG. 8 is a bar graph showing the denaturation temperature of hair swatches after comparative compositions and exemplary cosmetic composition according to aspects of the disclosure.
Figure 9:
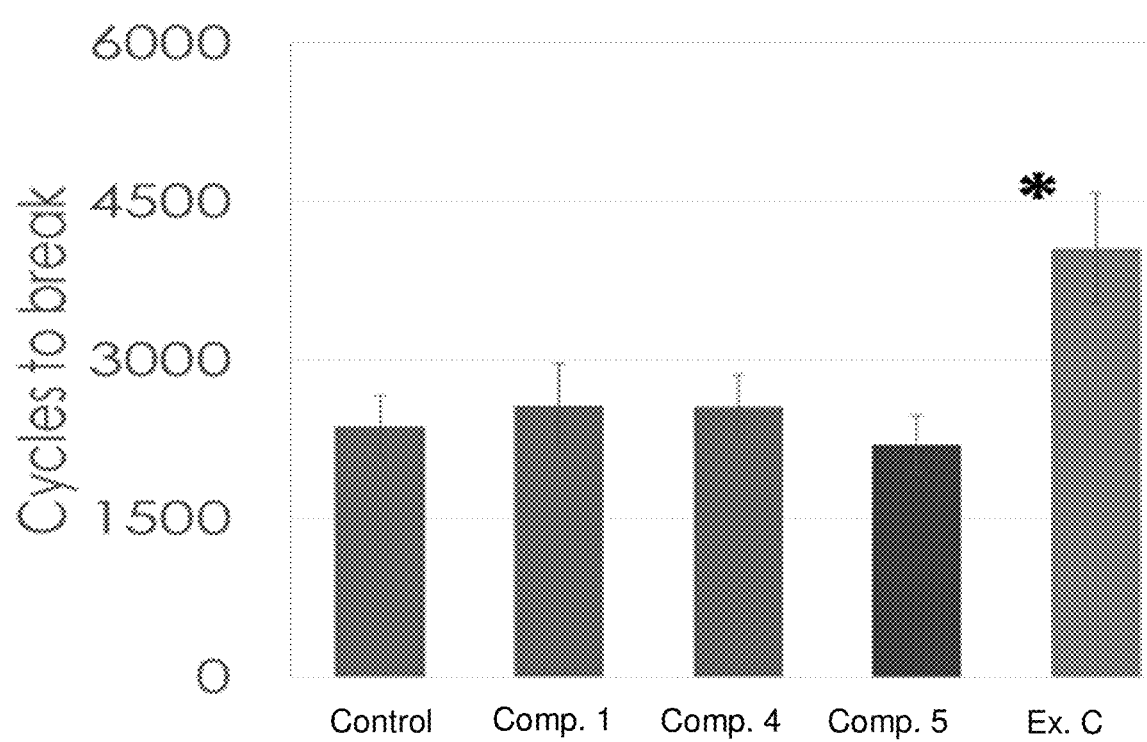
FIG. 9 is a bar graph showing the durability of hair swatches after comparative compositions and exemplary cosmetic composition in accordance with aspects of the disclosure.

The hair that was treated with Exemplary Composition C exhibited an improved thermal denaturation temperature and significantly improved durability as compared to hair treated with Comparative Compositions 1, 4, and 5, and the Control, as seen in FIGS. 8 and 9.

Example 7

The thermal denaturation temperature and durability effects imparted by Exemplary Compositions D-G in comparison to the effects imparted by Comparative Composition 1 and a Control. Exemplary Compositions D-G and Comparative Composition 1 were applied to bleached hair swatches. The bleached hair swatches were washed with a conventional sulfate-based shampoo and rinsed before the application of Exemplary Compositions D-G and Comparative Composition 1 in an amount of about 0.4 gram of the respective cosmetic composition per gram of hair swatch. The hair swatches were massaged to uniformly spread the respective cosmetic formulations on the hair swatches. After about 1 minute, the hair swatches were rinsed with water. A control was prepared according to the above procedure, except that a cosmetic composition was not applied to the respective hair swatch after the conventional sulfate-based shampoo.

The hair was then assessed to evaluate effect of E Exemplary Compositions D-G and Comparative Composition 1 on the thermal denaturation temperature, which corresponds to cross-link density, and durability of the hair in view of the Control. The thermal denaturation temperature and durability of the hair was determined as discussed in Example 3.

Figure 10:
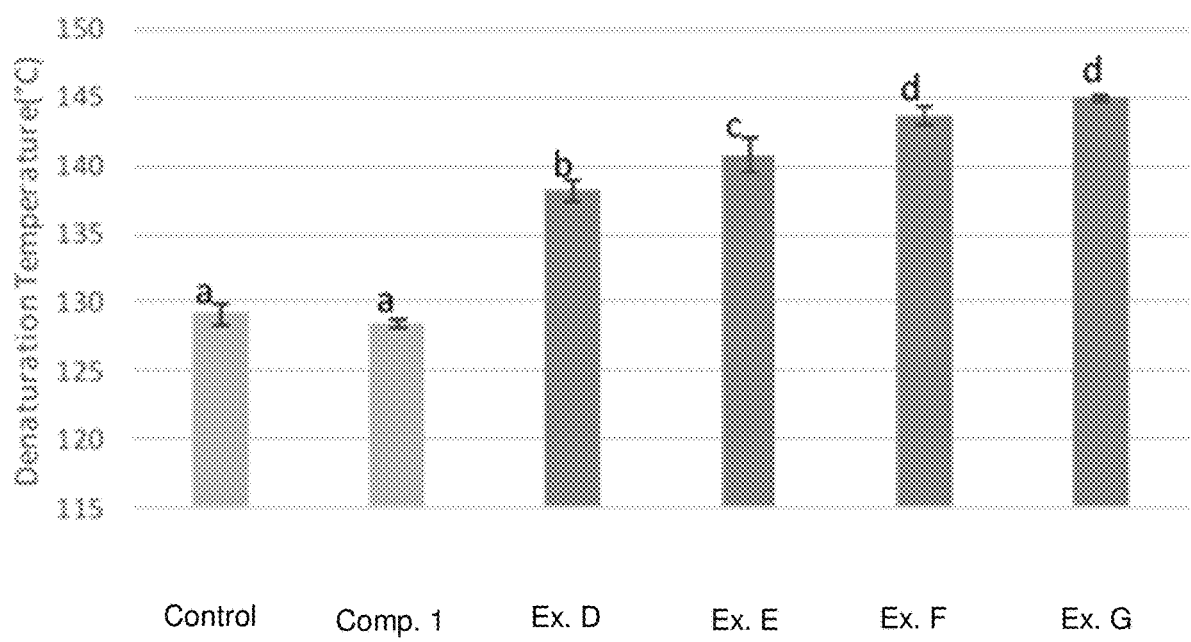
FIG. 10 is a bar graph showing the denaturation temperature of hair swatches after comparative compositions and exemplary cosmetic composition according to aspects of the disclosure.
Figure 11:
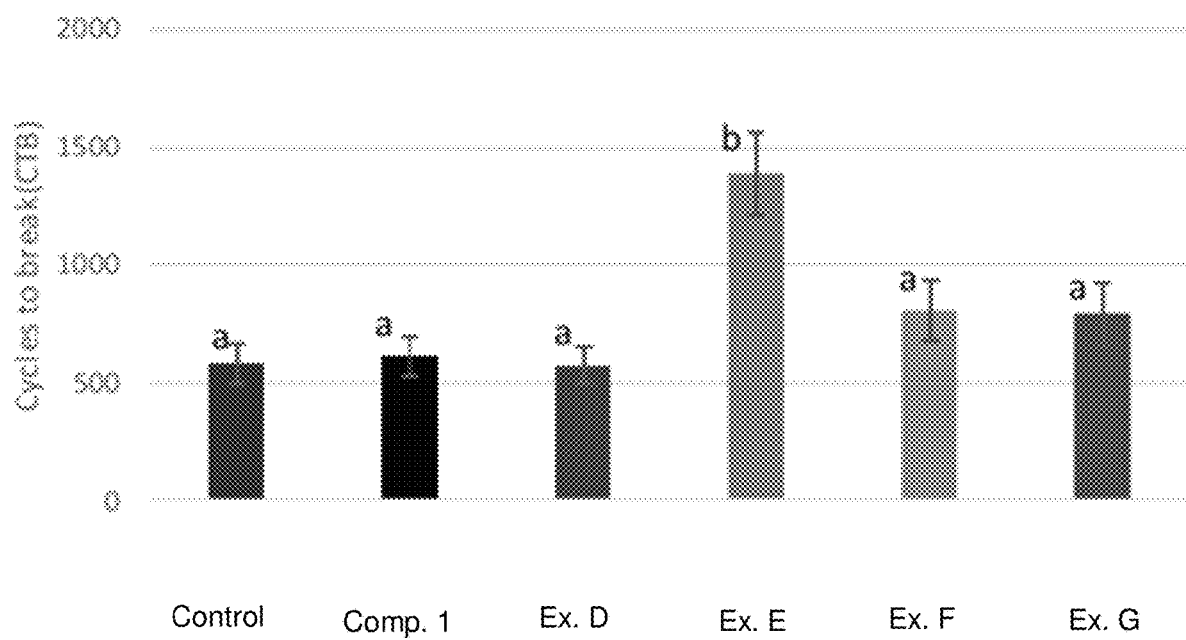
FIG. 11 is a bar graph showing the durability of hair swatches after comparative compositions and exemplary cosmetic composition in accordance with aspects of the disclosure.

As seen in FIG. 10, Exemplary Compositions D-G exhibited improved thermal denaturation temperature as compared to hair treated with Comparative Composition 1 and the control. The hair treated with Exemplary Composition E exhibited surprisingly improved durability, as seen in FIG. 11.

What is claimed is:

1. A cosmetic composition comprising:
   (a) about 50 to about 85 wt. % of propylene glycol;
   (b) about 15 to about 50 wt. % of ethanol;
      wherein a weight ratio of (a) to (b) is from 20:1 to 1:20 ((a):(b));
   (c) about 0.1 to about 10 wt. % of one or more cationic surfactants;
   (d) about 0.1 to about 20 wt. % of one or more fatty compounds; and
   (e) about 1 to about 15 wt. % of a combination of:
      (i) citric acid, and
      (ii) a urea compound,
         wherein a mole ratio of (i) to (ii) is about 10:0.5 to about 0.5:10 ((i):(ii)), and all weight percentages are based on the total weight of the cosmetic composition.

2. The cosmetic composition of claim 1, wherein the combination of the citric acid and urea compound was added as a deep eutectic solvent.

3. The cosmetic composition of claim 1, wherein the mole ratio of (i) to (ii) is about 8:1 to about 1:8 ((i):(ii)).

4. The cosmetic composition of claim 3, wherein the mole ratio of (i) to (ii) is about 6:1 to about 1:6 ((i):(ii)).

5. The cosmetic composition of claim 4, wherein the mole ratio of (i) to (ii) is about 5:1 to about 1:2 ((i):(ii)).

6. The cosmetic composition of claim 1, wherein the weight ratio of (i) to (ii) is about 12:1 to about 1:12 ((i):(ii)).

7. The cosmetic composition of claim 6, wherein the weight ratio of (i) to (ii) is about 10:1 to about 1:10 ((i):(ii))).

8. The cosmetic composition of claim 1 comprising about 3 to about 7 wt. % of the combination of (e).

9. The cosmetic composition of claim 1, wherein the urea compound is dimethyl urea, a hydroxyethyl urea, urea, or mixtures thereof.

10. The cosmetic composition of claim 1, wherein the cosmetic composition is a solubilized, non-emulsified composition until applied to wet or damp keratinous substrate or placed in contact with water, whereupon the composition forms a lamellar phase in situ.

11. The cosmetic composition of claim 1 wherein the one or more cationic surfactants are selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, stearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamidopropyidiethylamine, arachidamidoethyidiethylamine, arachidamidoethyidimethylamine, or a mixture thereof.

12. The cosmetic composition of claim 1, wherein the one or more fatty compounds are chosen from a fatty alcohol, a fatty ester, a fatty carbonate ester, a fatty ether, a fatty acid, a wax, an oil, a derivative thereof, or a mixture thereof.

13. The cosmetic composition of claim 12, wherein the fatty carbonate ester is chosen from dialkyl carbonates of formula: $R_1O(C=O)R_2$, wherein $R_1$ and $R_2$ are independently linear or branched, saturated or unsaturated alkyl chains having 1 to 30 carbon atoms.

14. The cosmetic composition of claim 12, wherein the fatty ester is chosen from cetyl ester, cetearyl octanoate, isopropyl myristate, isopropyl palmitate, $C_{12}$-$C_{15}$ alkyl benzoate, 2-ethylphenyl benzoate, isopropyl lanolate, hexyl laurate, diisopropyl adipate, isononyl isononanoate, oleyl erucate, 2-ethylhexyl palmitate, isostearyl isostearate, diisopropyl sebacate, octanoates, decanoates or ricinoleates of alcohols or polyalcohols, hydroxylated esters, dicaprylyl carbonate, pentaerythritol esters, diisostearyl malate, neopentyl glycol dioctanoate, dibutyl sebacate, di-$C_{12-13}$ alkyl malate, dicetearyl dimer dilinoleate, dicetyl adipate, diisocetyl adipate, diisononyl adipate, diisostearyl dimer dilinoleate, diisostearyl fumarate, or a mixture thereof.

15. The cosmetic composition of claim 12, wherein the fatty alcohol is chosen from decyl alcohol, undecyl alcohol, dodecyl alcohol, myristyl alcohol, lauryl alcohol, cetyl alcohol, stearyl alcohol, cetearyl alcohol, isostearyl alcohol, isocetyl alcohol, behenyl alcohol, linalool, oleyl alcohol, cis-4-t-butylcyclohexanol, isotridecyl alcohol, myricyl alcohol, or a mixture thereof.

16. The cosmetic composition of claim 12, wherein the fatty ether is chosen from olyoxyethylene cetyl/stearyl ether, polyoxyethylene cholesterol ether, polyoxyethylene laurate or dilaurate, polyoxyethylene stearate or distearate, polyoxyethylene lauryl or stearyl ether, dicaprylyl ether, dicetyl ether distearyl ether, dodecyl ether, dilauryl ether, dimyristyl ether, diisononyl ether, or a mixture thereof.

17. The cosmetic composition of claim 12, wherein the fatty acid is chosen from myristic acid, lauric acid, palmitic acid, stearic acid, behenic acid, arachidonic acid, oleic acid, isostearic acid, sebacic acid, or a mixture thereof.

18. The cosmetic composition of claim 1 being substantially free of water.

19. The cosmetic composition of claim 1, wherein the composition is a hair care composition.

20. A cosmetic composition for treating keratinous substrates comprising:
   (a) about 50 to about 85 wt. % of one or more polyols chosen from ethylene glycol, propylene glycol, butylene glycol, hexylene glycol, pentylene glycol, diethylene glycol, dipropylene glycol, 1,3 propanediol, glycerin, or a mixture thereof;
   (b) about 15 to about 50 wt. % of one or more monoalcohols having from 2 to 6 carbon atoms;
      wherein a weight ratio of (a) to (b) is from 20:1 to 1:20 ((a):(b));
   (c) about 0.1 to about 10 wt. % of one or more cationic surfactants;
   (d) about 0.1 to about 15 wt. % of one or more fatty compounds chosen from a fatty alcohol, a fatty ester, a fatty ether, a fatty acid, a wax, an oil, a derivative thereof, and a mixture thereof; and (e) about 1 to about 15 wt. % of a combination of:
  (i) citric acid, and
  (ii) a urea compound chosen from dimethyl urea, hydroxyethyl urea, urea, and a mixture thereof,
    wherein a mole ratio of (i) to (ii) is about 10:0.5 to about 0.5:10 ((i):(ii)), and all weight percentages are based on the total weight of the cosmetic composition.

21. The cosmetic composition of claim 20, wherein the mole ratio of (i) to (ii) is about 5:1 to about 1:2 ((i):(ii)).

22. A method for treating hair comprising:
(I) optionally, applying a shampoo to hair;
(II) optionally, rinsing the hair to remove at least a portion of the shampoo;
(III) applying the cosmetic composition of claim 1 to the hair; and
(IV) optionally, rinsing the hair to remove at least a portion of the cosmetic composition.

23. A method for treating hair comprising:
(I) optionally, applying a shampoo to hair;
(II) optionally, rinsing the hair to remove at least a portion of the shampoo;
(III) applying the cosmetic composition of claim 20 to the hair; and
(IV) optionally, rinsing the hair to remove at least a portion of the cosmetic composition.

* * * * *